(12) United States Patent
Feng et al.

(10) Patent No.: US 12,258,386 B2
(45) Date of Patent: Mar. 25, 2025

(54) HUMANIZED ANTI-A β MONOCLONAL ANTIBODY AND APPLICATION THEREOF

(71) Applicant: CHANGCHUN GENESCIENCE PHARMACEUTICAL CO., LTD., Changchun (CN)

(72) Inventors: Xiao Feng, Changchun (CN); Yangqiu Liang, Changchun (CN); Lei Jin, Changchun (CN); Dawei Sun, Changchun (CN); Tao Wang, Changchun (CN); Liang Xiao, Changchun (CN); Shuang Liu, Changchun (CN); Yuheng Chen, Changchun (CN); Zhengyi Li, Changchun (CN)

(73) Assignee: Changchun Genescience Pharmaceutical Co., Ltd., Jilin (CN)

( * ) Notice: Subject to any disclaimer, the term of this patent is extended or adjusted under 35 U.S.C. 154(b) by 785 days.

(21) Appl. No.: 17/427,589

(22) PCT Filed: Jan. 17, 2020

(86) PCT No.: PCT/CN2020/072629
§ 371 (c)(1),
(2) Date: Jul. 30, 2021

(87) PCT Pub. No.: WO2020/156222
PCT Pub. Date: Aug. 6, 2020

(65) Prior Publication Data
US 2022/0242937 A1  Aug. 4, 2022

(30) Foreign Application Priority Data
Feb. 1, 2019 (CN) .......................... 201910104326.1

(51) Int. Cl.
| A61K 39/395 | (2006.01) |
| A61K 39/00 | (2006.01) |
| A61K 47/68 | (2017.01) |
| A61P 25/28 | (2006.01) |
| C07K 16/00 | (2006.01) |
| C07K 16/18 | (2006.01) |

(52) U.S. Cl.
CPC ............. *C07K 16/18* (2013.01); *A61K 39/00* (2013.01); *A61K 39/0007* (2013.01); *A61K 39/395* (2013.01); *A61K 47/6843* (2017.08); *A61P 25/28* (2018.01); *A61K 2039/505* (2013.01); *C07K 2317/24* (2013.01); *C07K 2317/52* (2013.01); *C07K 2317/565* (2013.01); *C07K 2317/567* (2013.01); *C07K 2317/76* (2013.01); *C07K 2317/92* (2013.01)

(58) Field of Classification Search
CPC ................ C07K 2317/24; C07K 16/18; C07K 2317/92; C07K 2317/34; C07K 2317/56; C07K 2317/565; C07K 2317/55; C07K 14/4711; A61K 2039/505; A61K 39/007; A61K 39/00; A61K 39/46432; A61P 25/00; A61P 25/28
See application file for complete search history.

(56) References Cited

U.S. PATENT DOCUMENTS

| 2012/0064065 A1 | 3/2012 | Preifer et al. |
| 2015/0024512 A1 | 1/2015 | Willbold |
| 2022/0242936 A1* | 8/2022 | Feng ...................... A61P 17/00 |

FOREIGN PATENT DOCUMENTS

| CN | 101531717 A | 9/2009 |
| CN | 101622275 A | 1/2010 |
| CN | 101802007 A | 8/2010 |
| CN | 1798766 B | 5/2012 |
| CN | 103179981 A | 6/2013 |
| CN | 105461808 A | 4/2016 |
| CN | 106928354 A | 7/2017 |
| CN | 107561264 A | 1/2018 |
| CN | 108250296 A | 7/2018 |
| CN | 108341871 A | 7/2018 |
| CN | 111518206 B | 3/2022 |
| EP | 0783104 A1 | 7/1997 |
| EP | 1636268 B1 | 2/2012 |
| EP | 3575322 A1 | 4/2019 |
| RU | 2551782 C2 | 5/2015 |
| RU | 2575095 C2 | 2/2016 |
| WO | 03077858 A2 | 3/2002 |
| WO | 2003077858 A2 | 9/2003 |
| WO | 2009033309 A1 | 3/2009 |

OTHER PUBLICATIONS

Burgess et al. J of Cell Bio. 1990, 111:2129-2138.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
MacCallum et al., J. Mol. Biol., 1996; 262: 732-745.*
Pascalis et al., The Journal of Immunology, 2002; 169: 3076-3084.*
Casset et al., BBRC, 2003; 307: 198-205.*
Vajdos et al. (J. Mol. Biol. 2002; 320: 415-428.*
Holm et al., Mol. Immunol., 2007; 44: 1075-1084.*
Chen et al., J. Mol. Bio., 1999; 293: 865-881.*
Wu et al., J. Mol. Biol., 1999; 294:151-162.*
Van Dyck, "Anti-Amyloid-Beta Monoclonal Antibodies for Alzheimer's Disease: Pitfalls and Promise", Biological Psychiatry, Feb. 15, 2018, 9 pages.

(Continued)

*Primary Examiner* — Chang-Yu Wang
(74) *Attorney, Agent, or Firm* — POLSINELLI PC

(57) ABSTRACT

Provided are a humanized anti-Aβ monoclonal antibody and use thereof. The humanized anti-Aβ monoclonal antibody provided can inhibit the polymerization of Aβ monomers, protect nerve cells from the toxicity of Aβ, and have a certain effect on improving the cognitive learning and memory ability of Alzheimer's dementia model mice, and can be used for the treatment and diagnosis of diseases and disorders related to amyloidosis, such as Alzheimer's disease.

9 Claims, 4 Drawing Sheets
Specification includes a Sequence Listing.

(56) References Cited

OTHER PUBLICATIONS

Chen et al., "Effects of new drugs anti-ABeta monoclonal antibodies on learning and memory in Alzheimer's disease mice", Journal of Xinjiang Medical University, vol. 37, No. 4, Apr. 2014 (English Abstract).
Prins N.D. et al, "Treating Alzheimer's disease with monoclonal antibodies: current status and outlook for the future, Alzheimer's Research & Therapy", 2013.
Stains et al., "Molecules that Target beta-Amyloid", ChemMedChem, 2007, vol. 2, N12, pp. 1674-1692.
Russian Office Action issued in corresponding Russian Patent Application No. 2021122154, mailed Jan. 21, 2022.
Rudikoff et al., "Single amino acid substitution altering antigen-binding specificity", Proc. Natl. Acad. Sci. USA, vol. 78, pp. 1979-1983, Mar. 1982.
Agadjanyan, M. G.: "Humanized monoclonal antibody armanezumab specific to N-terminus of pathological tau: charaterization and therapeutic potency", Molecular Neurodegeneration, vol. 12, No. 33, May 5, 2017 (May 5, 2017), pp. 1-18, XP055388653, DOI: 10.1186/s13024-017-0172-1.
Kabat et al.: "Sequences of proteins of immunological interest", 1991, US Department of Health and Human Services, Nih.
Niels D Prins; Philip Scheltens: "Treating Alzheimer's disease with monoclonal antibodies: current status and outlook for the future", Alzheimer's Research & Therapy., vol. 5, No. 6, Nov. 11, 2013 (Nov. 11, 2013), pp. 56, XP021193607, DOI: 10.1186/alzrt220.
Extended European Search Report regarding application 20749200.0, dated Jan. 26, 2023, 14 pages.
Cattepoel, s. et al, Chronic Intranasal Treatment with an Anti-Aβ30-42 scFv Antibody Ameliorates Amyloid Pathology in a Transgenic Mouse Momdel of Alzheimer's Disease, PLoS One, 2011, vol. 6, Issue 4, e18296, pp. 1-13.
Lafaye, P. et al, Single-domain antibodies recognize selectively small oligomeric forms of amyloid β, prevent Aβ-induced neurotoxicity and inhibit fibril formation, Molecular Immunology, 2009, vol. 46, pp. 695-704.
Vandyck, C.H., Anti-Amyloid-B Monoclonal Antibodies for Alzheimer's Disease: Pitfalls and Promise, Socieity of Biological Psychiatry, Feb. 15, 2018, vol. 83, pp. 311-319.
Russian Office Action regarding application No. 20121122154 dated Jun. 20, 2022, 3 pages.
Esparza, T.J. et al., Soluble Amyloid-beta Aggregates from Human Alzheimer's Disease Brains, Scientific Reports, 2016, vol. 6, pp. 1-16.
Chinese application CN1798766B, published May 30, 2012, English version EP1636268B, 92 pages.
Chinese application CN103179981A, published Jun. 26, 2013, English version US20120064065A1, 54 pages.
Chinese application CN108341871A, published Jul. 31, 2018, English version EP3575322, 54 pages.
PCT/CN2020/072629 English translated International Search Report dated Apr. 15, 2020, 7 pages.
Agadjanyan, M.G. et al, Humanized monoclonal antibody armanezumab specific to N-terminus of pathological tau: characterization and therapeutic potency, Molecular Neurodegeneration, 2017, vol. 12, No. 33, 18 pages.
Prins, N.D. and Scheltens, P., Treating Alzheimer's disease with monoclonal antibodies: current status and outlook for the future, Alzheimer's Research & Therapy, 2013, vol. 5, No. 56, 6 pages.

\* cited by examiner

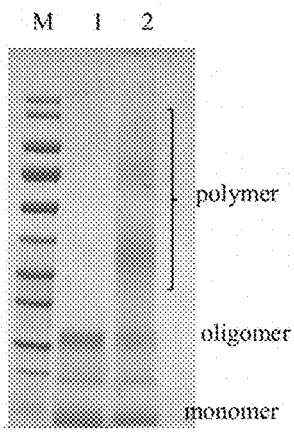
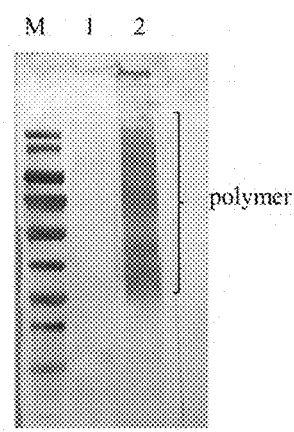
Fig. 1(A)   Fig. 1(B)
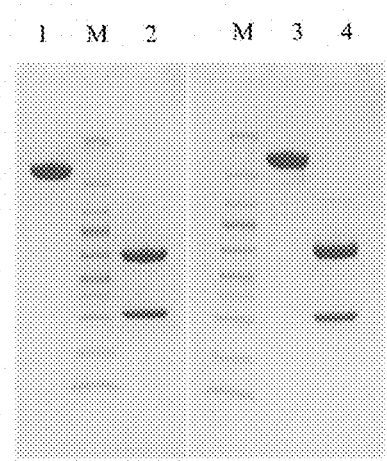
Fig. 2(A)   Fig. 2(B)
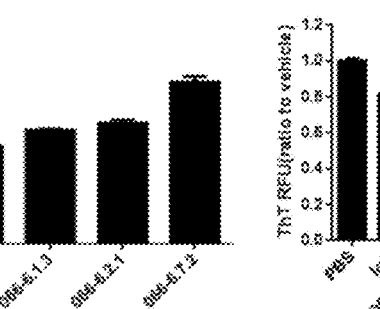
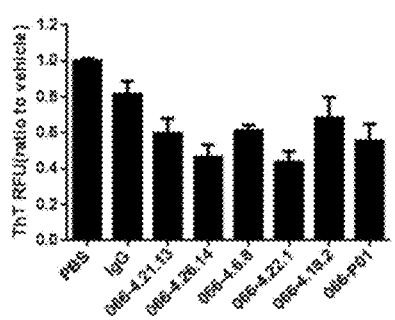
Fig. 3(A)   Fig. 3(B)

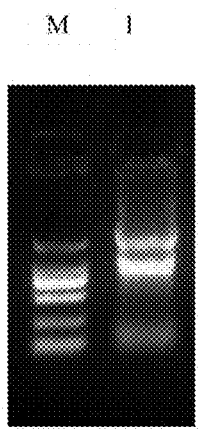
Fig. 7
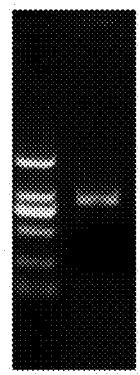   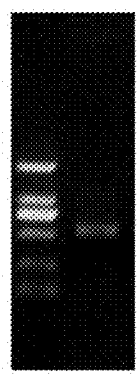
Fig. 8(A)    Fig. 8(B)
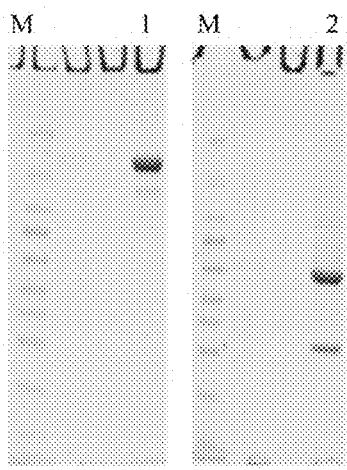
Fig. 9(A)    Fig. 9(B)

HUMANIZED ANTI-Aβ MONOCLONAL ANTIBODY AND APPLICATION THEREOF

CROSS REFERENCE TO RELATED APPLICATIONS

The present application is the U.S. National Phase under 35 U.S.C. § 371 of International Application No. PCT/CN2020/072629, filed Jan. 17, 2020, which claims the priority of the Chinese patent application filed with the Chinese Patent Office on Feb. 1, 2019, with the application No. 201910104326.1 and the invention title of "Humanized anti-Aβ monoclonal antibody and use thereof", the entire contents of each of which are herein incorporated in the present application by reference.

SEQUENCE LISTING

A Sequence Listing submitted herewith as an ASCII text file via EFS-Web is hereby incorporated by reference in accordance with 35 U.S.C. § 1.52 (e). The name of the ASCII text file for the Sequence Listing is IEC210121_Sequence Listing_EN. TXT, and the size of the ASCII text file is 33 KB.

TECHNICAL FIELD

The present disclosure relates to the technical field of antibody medicines, in particular to a humanized anti-Aβ monoclonal antibody and use thereof.

BACKGROUND ART

Aβ

Amyloid β (Aβ) is encoded by the human chromosome 21 gene, contains 39-43 amino acids, has a β-sheet structure, is hydrophobic, and has a molecular weight of 4 KDa. Aβ is derived from the residue polypeptide produced by the fragmentation of amyloid precursor protein (APP) by proteolytic enzymes. APP can be decomposed by α-, β- and γ-proteases, and the products after decomposition have different biological functions. Among them, Aβ is produced by the continuous action of β-protease and γ-protease. The C-terminus of Aβ is produced by γ-protease, and a large number of residue subtypes with 39-43 amino acids are produced by cutting APP at the transmembrane region. The most common of all residue subtypes are $Aβ_{40}$ and $Aβ_{42}$. The former is typically formed by cutting APP at the endoplasmic reticulum, while the latter is formed in the trans-Golgi network.

Pathological Mechanism of Aβ

It is currently known that all nerve cells, including neurons, astrocytes, microglia and endothelial cells, in the central nervous system (CNS) can express APP and produce Aβ. Under normal physiological conditions, APP is hydrolyzed by α-secretase to produce a soluble sAPPα fragment. This fragment contains the extracellular region of APP and the C-terminus with 83 amino acids located on the cell membrane. sAPPα can regulate the excitability of neurons, improve the plasticity, learning and memory of synapses, and enhance the resistance of neurons to oxidative and metabolic stress. Under neuropathological conditions, APP is first hydrolyzed by β-secretase 1 (BACE) to produce a sAPPβ fragment and a peptide fragment with 99-amino acids (C99) connected to the cell membrane. Subsequently, the C99 peptide is subjected to the action of γ-secretase to produce Aβ. Different from sAPPα, Aβ can cause the loss of nerve synapse function, reduce the plasticity of neurons, change cell energy metabolism, induce oxidative stress response and mitochondrial dysfunction, thereby causing the imbalance of intracellular calcium ions. The formation, accumulation and deposition of Aβ, especially $Aβ_{42}$, may cause neurotoxicity and neurodegenerative diseases, and also play an important role in the pathogenesis of Alzheimer's disease (AD).

Aβ and Alzheimer's Disease (AD)

As one of the main intracerebral pathological marker proteins of Alzmer's disease, the formation, deposition and degradation of Aβ run through the whole pathological process of AD. Aβ is divided into two types: soluble and insoluble. Soluble Aβ itself has no neurotoxicity, but shows neurocytotoxicity after becoming insoluble precipitates upon formation of filamentous fiber aggregates by β-sheet. The primary structure of human Aβ is a determinant factor of neurotoxicity. According to reports in the literature, the neurotoxicity of Aβ is mainly reflected in the following four aspects: cholinergic neuron damage, nerve cell apoptosis, peroxidative damage and inflammatory response.

Cholinergic Neuron Damage

The damage and loss of a large number of cholinergic system neurons and nerve synapses in the anterior basal projecting to the hippocampus and cortex are the main reasons for the decline of memory and cognitive ability of AD patients. Aβ activates protein kinase GSK-3/glycogen synthase kinase-3β, which causes the phosphorylation of tau protein and mitochondrial pyruvate dehydrogenase, reduces the enzyme activity, and reduces the conversion of pyruvate into acetyl coenzyme A (actyl coenzyme A), thereby reducing the synthesis of acetylcholine (ACh), inhibiting succinate dehydrogenase, reducing energy supply, causing the damage, degeneration and transmitter transmission disorder of cholinergic neurons and synapses, and decreasing the activity of the cholinergic system. The reduction of ACh in turn leads to an increase in the production of Aβ, which in turn forms a vicious circle.

Nerve Cell Apoptosis

The main characteristic of AD is the decrease in the number of neurons in the cortex and hippocampus. When Aβ aggregates into a β-sheet folding structure, its neurotoxicity is significantly enhanced, and it can induce the apoptosis of nerve cells. This is an important reason for the lack of selective neurons and synapses in AD. The fibrous and aggregated Aβ and APP and other transmembrane receptors interact and cross-link through secretory pathways on the cell surface, leading to the inhibition and abnormal activation of signal transduction pathways, thereby starting the apoptosis of nerve cells. The Aβ-induced $Ca^{2+}$ imbalance in the internal environment stimulates NMDA receptors or changes the membrane permeability through free radical damage effect, causing the $Ca^{2+}$ influx to activate glutamate receptors, and causing the overexcitation and death of glutamatergic neurons. In addition, Aβ may also cause the increase of NO synthesis, thereby inducing the apoptosis of neuronal cells.

Peroxidative Damage

Aβ may cause oxidative stress in many ways. Oxidative stress caused by the increase of free radicals induced by Aβ is an important reason. The toxicity of Aβ is mediated by $H_2O_2$, and Aβ increases the accumulation of $H_2O_2$ in the body through the receptor of advanced glycation endoproduct (RAGE), causing oxidative damage and causing cell death. In addition, oxidative stress causes the microglia to proliferate and migrate along the Aβ concentration gradient, leading to aggregation of microglia around senile plaques, forming neuritic plaques, and generating more reactive oxygen free radicals. Aβ can also increase lipid peroxidation. H₂O₂ is not only a source of hydroxyl free radicals, but also increases the abnormal expression of nuclear factor κB (NF-κB) protein, which causes nerve cell membrane damage and leads to neuronal degeneration.

Inflammatory Reaction

AD patients usually have inflammatory reaction in the brain. Glial cells proliferate around plaques and neurofibrillary tangles. Aβ may stimulate the release of a series of inflammatory proteins with strong neurotoxicity. For example, Aβ activates astrocytes and microglia to release inflammatory cytokines, such as NO, interleukin-1 (IL-1, IL-1 may cause abnormality in the production of cytoskeleton protein-neurofilament protein, thereby impairing the function of neurons), interleukin-6 (IL-6, IL-6 increases the overexpression of ADP and promotes the formation of Aβ, while Aβ may induce the expression of IL-6 in microglia, thereby forming a vicious circle in the immunopathological process of AD), tumor necrosis factor-α (TNF-α, TNF-α is involved in the pathological process of AD through the most important apolipoprotein ApoE of CNS), γ-interferon (γ-IFN), β-antitrypsin (ACT), complement C1, C3 and chemokines, adhesion factors, etc. Many inflammatory factors induce inflammation, promote the generation of free radicals, oxidative stress, resulting degeneration and necrosis of nerve cells.

Drugs and Therapeutic Mechanisms for Aβ Target Intervention

Based on the above, the toxicity of Aβ to neurons is an important factor in the occurrence of AD. Therefore, by inhibiting the production of Aβ and accelerating its clearance, the disease process of AD can be stopped, and the symptoms of the disease can be alleviated. The drugs currently being developed and used in clinic are also based on the production and clearance mechanism of Aβ, which include the following parts.

1. Inhibiting β- and γ-Secretases

The hydrolysis of APP by β-secretase is the initial stage of amyloid production. Inhibiting the activity of β-secretase can inhibit the production of Aβ, but it may cause greater side effects. Because in addition to APP, β-secretase has numerous substrates, and the hydrolysis of these substrates plays an important role in the plasticity of neurons and synapses in the nervous system. Clinically, β-secretase inhibitors, such as E2609 (clinical trial ID # NCT01600859), MK-8931 (NCT01739348) and LY2886721 (NCT01807026, NCT01561430) all can reduce Aβ levels in human cerebrospinal fluid by 80-90%, but currently there is still no β-secretase inhibitor on the market.

The hydrolysis of APP by γ-secretase is the last step in the production of amyloid, which directly produces Aβ40 and Aβ42 fragments. Therefore, it is also considered that the inhibition of γ-secretase may effectively inhibit the production of Aβ, so as to achieve the purpose of treating AD. However, in addition to hydrolyzing APP, γ-secretase also hydrolyzes other substrate proteins, including Notch protein. Notch protein is important for cell proliferation, differentiation and intercellular signal transduction. Semagacestat (LY450139) as a γ-secretase inhibitor has been clinically tested in 3000 patients (NCT00762411, NCT01035138, NCT00762411). The results of the test showed that the subjects' cognition did not improve, but deteriorated, and was accompanied by side effects such as weight loss, increased skin cancer probability, and high risk of infection. Other γ-secretase inhibitors, such as Avagacestat, have also failed in clinical trials (NCT00810147, NCT00890890, NCT00810147, NCT01079819). The selective γ-secretase modulator (SGSM) can theoretically avoid the side effects caused by the total inhibition of γ-secretase, and only inhibit the hydrolysis pathway of APP without interfering with other signal channels, such as the hydrolysis of Notch protein. Some non-steroidal anti-inflammatory drugs, such as ibuprofen, sulindac, indomethacin, and flurbiprofen, can regulate the level of γ-secretase, and can reduce the level of Aβ42 in in vivo and in vitro activity experiments. Although such drugs have been shown to relieve mild cognitive impairment and reduce the level of inflammatory factors in the cerebrospinal fluid, long-term use of non-steroidal anti-inflammatory drugs for the treatment of AD still needs to be clinically verified.

2. Inhibiting AP Aggregation

Inhibition of senile plaque can be achieved by interfering with or antagonizing the accumulation of Aβ. For example, 3-Amino-1-propane sulfonic acid (3-APS, Alzhemed, tramiprosate) interferes with the interaction between dissoluble Aβ and endogenous aminodextran, in which the later can promote the formation and precipitation of Aβ amyloid fibers, thereby inhibiting the accumulation of Aβ. However, the results of the Phase III clinical trial of 3-APS were not satisfactory, which led to the suspension of the trial. Other anti-Aβ aggregation drugs have also failed in phase II and phase III clinical trials, including Colostrinin, which could inhibit Aβ aggregation and neutralize the neurotoxicity of Aβ in an in vitro test, and could also improve the cognition ability of mice in an in vivo test, but it did not achieve satisfactory results in the clinical phase II trial. Scylloinositol (ELND005) is an oral anti-Aβ aggregation drug, and the mouse experiments have shown that Scyllo-inositol could reduce the toxicity of Aβ, but did not achieve the expected results in the 18-month phase II clinical trial for patients with mild to moderate AD.

3. Promoting the Clearance of Aβ Deposition and Polymer

There are three main ways to remove Aβ deposition and polymer: activating the activity of amyloid plaque degrading enzymes; regulating the transport of Aβ in the brain and peripheral circulation; and anti-Aβ immunotherapy.

The deposition and polymer of Aβ can be degraded by a variety of proteolytic enzymes, including plasmin, endothelin-converting enzyme, angiotensin-converting enzyme, metalloproteinase, etc. The levels of these enzymes in the brains of AD patients are relatively low, but due to the lack of specificity for these enzymes, no such drugs have entered the clinic at present.

The transport of Aβ between the central nervous system and the peripheral circulatory system is regulated by apolipoprotein. Low-density lipoprotein receptor-related protein (LRP-1) can promote the flow of Aβ from the brain into the blood. The receptor for advanced glycation end products (RAGE) can assist Aβ to pass through the blood-brain barrier. This treatment mechanism is to reduce the load of amyloid in the brain by restricting Aβ from entering the peripheral circulation. So far, only RAGE inhibitors/modulators have entered clinical trials, including PF-0449470052 and TTP4000. The former failed in phase II clinical trials, while the latter did not have reliable data to show that the expected results were achieved in phase I clinical trials.

Anti-Aβ antibodies can neutralize the toxicity of Aβ and improve the cognition of transgenic animals. Anti-Aβ antibodies have become a hot topic in AD treatment. Anti-Aβ antibodies mainly aim at the early treatment of AD, as well as the treatment of mild to moderate AD. This is also related to the pathogenic mechanism of Aβ, that is, once neurons are injured, it is difficult to reverse and repair them, therefore, the early removal of Aβ may more effectively treat and alleviate AD.

4. Aβ Target Antibodies Currently Undergoing Clinical Trials

There are currently 15 anti-Aβ antibody drugs undergoing clinical trials. In comparison, Aducanumab, Gantenerumab and Solanezumab have advanced rapidly and have entered phase III clinical trials. As mentioned in the mechanism, various companies have targeted mild Alzheimer's disease as their indications.

Although there is a certain theoretical knowledge in the field of treatment and prevention of Alzheimer's disease, there is still a need to improve the composition and method for the treatment and/or prevention of the disease, and there is a need for antibodies and treatments that can target Aβ. Although some humanized monoclonal antibodies with great therapeutic advantages have been obtained, it is not an easy task to screen out humanized monoclonal antibodies with the required properties and functions. In reality, there is still an urgent need for such humanized monoclonal antibodies.

Contents of the Present Disclosure

In view of this, the technical problem to be solved by the present disclosure is to provide a humanized anti-Aβ monoclonal antibody and use thereof, and also provide a carrier and host cell for a nucleotide encoding the monoclonal antibody and use thereof. From the sequence of the variable region of the antibody gene involved in the present disclosure, a full-length antibody molecule can be constructed, which can be used as a drug for treatment and diagnosis of an amyloidosis-related disease and disorder (such as Alzheimer's disease) in clinic.

In order to achieve the above-mentioned purpose of the present disclosure, the present disclosure provides the following technical solutions.

The present disclosure provides an anti-Aβ humanized monoclonal antibody, in which (I) the amino acid sequences of three heavy chain CDR regions of the monoclonal antibody are the amino acid sequences set forth in SEQ ID NOs: 1, 2 and 3, respectively; and (II) the amino acid sequences of three light chain CDR regions of the monoclonal antibody are the amino acid sequences set forth in SEQ ID NOs: 4, 5 and 6, respectively;

or (III) the amino acid sequences are the amino acid sequences obtained from the amino acids of (I) or (II) via substitution, deletion or addition of one or more amino acids, and are the amino acid sequences having the same function as the amino acid sequence of (I) or (II);

further, the function comprises two or three functions selected from the group consisting of inhibition of Aβ polymerization, improvement of cognitive learning and memory ability in an Alzheimer's dementia model, and cytotoxic protective activity;

or (IV) the amino acid sequences are the amino acid sequences having at least 97% homology with the amino acid sequences of (I), (II) or (III).

Further, the monoclonal antibody of the present disclosure has an antigen binding epitope of Aβ$_{30-42}$.

In some specific embodiments of the present disclosure, the present disclosure provides a humanized anti-Aβ monoclonal antibody, wherein:

its heavy chain comprises three CDR regions, in which at least one of the CDR regions has an amino acid sequence that is the amino acid sequence as shown in SEQ ID NO: 1, 2 or 3, or an amino acid sequence that has at least 97% homology with the amino acid sequence;

its light chain comprises three CDR regions, in which at least one of the CDR regions has an amino acid sequence that is the amino acid sequence as shown in SEQ ID NO: 4, 5 or 6, or an amino acid sequence that has at least 97% homology with the amino acid sequence.

In some specific embodiments of the present disclosure, the three heavy chain CDR regions of the monoclonal antibody have amino acid sequences that are the amino acid sequences as shown in SEQ ID NOs: 1, 2 and 3, respectively;

the three light chain CDR regions of the monoclonal antibody have amino acid sequences that are the amino acid sequences as shown in SEQ ID NOs: 4, 5 and 6, respectively.

```
Therein, the sequence shown in SEQ ID NO: 1 is SYAMS;

the sequence shown in SEQ ID NO: 2 is
SISTTSNTYYPDSVKG;

the sequence shown in SEQ ID NO: 3 is GVITNQAWFAY;

the sequence shown in SEQ ID NO: 4 is RASQSISNNLH;

the sequence shown in SEQ ID NO: 5 is YASQSIS;

the sequence shown in SEQ ID NO: 6 is QQSNSWPLT.
```

In some specific embodiments of the present disclosure, the present disclosure provides a monoclonal antibody, in which (V) the amino acid sequences of 4 heavy chain FR regions of the monoclonal antibody are the amino acid sequences set forth in SEQ ID NOs: 7, 8, 9 and 10, respectively; and (VI) the amino acid sequences of 4 light chain FR regions of the monoclonal antibody are the amino acid sequences set forth in SEQ ID NOs: 11, 12, 13 and 14, respectively;

or (VII) the amino acid sequences are the amino acid sequences obtained from the amino acids of (V) or (VI) via substitution, deletion or addition of one or more amino acids, and are the amino acid sequences having the same function as the amino acid sequences of (V) or (VI);

further, the function comprises two or three functions selected from the group consisting of inhibition of Aβ polymerization, improvement of cognitive learning and memory ability in an Alzheimer's dementia model, and cytotoxic protective activity;

or (VIII) the amino acid sequences are the amino acid sequences having at least 97% homology with the amino acid sequences of (V), (VI) or (VII).

In some specific embodiments of the present disclosure, its heavy chain comprises 4 FR regions, in which at least one of the FR regions has an amino acid sequence that is the amino acid sequence as shown in SEQ ID NO: 7, 8, 9 or 10, or an amino acid sequence that has at least 97% homology with the amino acid sequence;

its light chain comprises 4 FR regions, in which at least one of the FR regions has an amino acid sequence that is the amino acid sequence as shown in SEQ ID NO: 11, 12, 13 or 14, or an amino acid sequence that has at least 97% homology with the amino acid sequence.

In some specific embodiments of the present disclosure, the 4 heavy chain FR regions of the monoclonal antibody have amino acid sequences that are the amino acid sequence as shown in SEQ ID NOs: 7, 8, 9 and 10, respectively, or amino acid sequences that have at least 97% homology with the amino acid sequences;

the 4 light chain FR regions of the monoclonal antibody have amino acid sequences that are the amino acid sequence as shown in SEQ ID NOs: 11, 12, 13 and 14, respectively, or amino acid sequences that have at least 97% sequence homology with the amino acid sequences.

```
Therein, the sequence shown in SEQ ID NO: 7 is
EVQLVESGGGLVQPGGSLRLSCVASGFTFR;

the sequence shown in SEQ ID NO: 8 is
WVRQAPGKGLEWVA;

the sequence shown in SEQ ID NO: 9 is
RFTTSRDNSKNTVYLQMSSLRAEDTAVYYCGR;

the sequence shown in SEQ ID NO: 10 is
WGQGTLVTVSS;

the sequence shown in SEQ ID NO: 11 is
DIVLTQSPATLSVSPGERATLSC;

the sequence shown in SEQ ID NO: 12 is
WYQQKPGQAPRLLIK;

the sequence shown in SEQ ID NO: 13
GIPARFSGSGSGTDFTLTISSLQSEDFAVYFC;

the sequence shown in SEQ ID NO: 14 is
FGGGTKVEIK.
```

In some specific embodiments of the present disclosure, for the monoclonal antibody,
(IX) its heavy chain variable region has the amino acid sequence as shown in any one of SEQ ID NOs: 15 to 19; and (X) its light chain variable region has the amino acid sequence as shown in any one of SEQ ID NOs: 20 to 24;
or
(XI) its heavy chain variable region or its light chain variable region has the amino acid sequence is obtained from the amino acids of (IX) or (X) via substitution, deletion or addition of one or more amino acids, and are the amino acid sequence having the same function as the amino acid sequence of (IX) or (X);
further, the function comprises two or three functions selected from the group consisting of inhibition of AP polymerization, improvement of cognitive learning and memory ability in an Alzheimer's dementia model, and cytotoxic protective activity;
or
(XII) its heavy chain variable region or its light chain variable region has the amino acid sequence having at least 97% homology with the amino acid sequence of (IX), (X) or (XI).

In some specific embodiments of the present disclosure, its heavy chain variable region has the amino acid sequence as shown in any one of SEQ ID NOs: 15 to 19; and its light chain variable region has the amino acid sequence as shown in any one of SEQ ID NOs: 20 to 24.

In some specific embodiments of the present disclosure, the humanized anti-Aβ monoclonal antibody comprises:

a heavy chain variable region that has the amino acid sequence as shown in SEQ ID NO: 15, 16, 17, 18 or 19, and a light chain variable region that has the amino acid sequence as shown in SEQ ID NO: 20; or a heavy chain variable region that has the amino acid sequence as shown in SEQ ID NO: 15, 16, 17, 18 or 19, and a light chain variable region that has the amino acid sequence as shown in SEQ ID NO: 21; or a heavy chain variable region that has the amino acid sequence as shown in SEQ ID NO: 15, 16, 17, 18 or 19, and a light chain variable region that has the amino acid sequence as shown in SEQ ID NO: 22; or a heavy chain variable region that has the amino acid sequence as shown in SEQ ID NO: 15, 16, 17, 18 or 19, and a light chain variable region that has the amino acid sequence as shown in SEQ ID NO: 23; or a heavy chain variable region that has the amino acid sequence as shown in SEQ ID NO: 15, 16, 17, 18 or 19, and a light chain variable region that has the amino acid sequence as shown in SEQ ID NO: 24.

In some specific embodiments of the present disclosure, for the monoclonal antibody,
(XIII) its heavy chain variable region has the amino acid sequence as shown in SEQ ID NO: 16, and its light chain variable region has the amino acid sequence as shown in SEQ ID NO: 21; or
(XIV) its heavy chain variable region has the amino acid sequence as shown in SEQ ID NO: 16, and its light chain variable region has the amino acid sequence as shown in SEQ ID NO: 22; or
(XV) its heavy chain variable region has the amino acid sequence as shown in SEQ ID NO: 18, and its light chain variable region has the amino acid sequence as shown in SEQ ID NO: 21; or
(XVI) its heavy chain variable region has the amino acid sequence as shown in SEQ ID NO: 19, and its light chain variable region has the amino acid sequence as shown in SEQ ID NO: 20; or
(XVII) its heavy chain variable region has the amino acid sequence as shown in SEQ ID NO: 19, and its light chain variable region has the amino acid sequence as shown in SEQ ID NO: 21; or
(XVIII) its heavy chain variable region has the amino acid sequence as shown in SEQ ID NO: 19, and its light chain variable region has the amino acid sequence as shown in SEQ ID NO: 22.

In the present disclosure, the sequence that has at least 97% sequence homology is an amino acid sequence obtained by substitution, deletion or addition of one or more amino acids on the basis of the original sequence, wherein the more amino acids refer to 2, 3, 4 or 5 amino acids.

In some specific embodiments of the present disclosure, the monoclonal antibody further comprises a constant region, in which the monoclonal antibody has a heavy chain constant region that is any one of human IgG1, IgG2, IgG3, or IgG4; and the monoclonal antibody has a light chain constant region that is of κ type or λ type.

In some specific embodiments of the present disclosure, the anti-Aβ monoclonal antibody provided by the present disclosure has a heavy chain constant region that is human IgG1, and a light chain constant region that is a constant region of human κ chain.

The humanized anti-Aβ monoclonal antibody provided by the present disclosure can bind to human Aβ; in some embodiments, the affinity between the antibody and its target is characterized by Ka (association constant), Kd (dissociation constant), and KD (equilibrium dissociation solution);

and the KD value of the antibody provided by the present disclosure is not higher than 36.3 nM. The humanized anti-Aβ monoclonal antibody provided by the present disclosure can inhibit the polymerization of Aβ monomer, protect nerve cells from the toxicity of Aβ, and has a certain effect on improving cognitive learning and memory ability in Alzheimer's dementia model mice.

The present disclosure also provides nucleotides encoding the monoclonal antibody.

The present disclosure provides a nucleotide sequence encoding the heavy chain of the monoclonal antibody.

The present disclosure provides a nucleotide sequence encoding the light chain of the monoclonal antibody.

The present disclosure provides a nucleotide sequence encoding the heavy chain variable region of the monoclonal antibody.

Therein, the nucleotide sequence encoding the heavy chain variable region of the monoclonal antibody is shown in SEQ ID NOs: 25 to 29 or is a complementary sequence of SEQ ID NOs: 25 to 29.

In some specific embodiments of the present disclosure, the nucleotide has a nucleotide sequence that is obtained from the nucleotide sequence as shown in any one of SEQ ID NOs: 25 to 29 via substitution, deletion or addition of one or more nucleotides and has the same or similar function as the nucleotide sequence as shown in any one of SEQ ID NOs: 25 to 29.

In some specific embodiments of the present disclosure, for the nucleotide sequence that is obtained from the nucleotide sequence as shown in any one of SEQ ID NOs: 25 to 29 via substitution, deletion or addition of one or more nucleotides, the more nucleotides refer to 2, 3, 4 or 5 nucleotides.

The present disclosure provides a nucleotide sequence encoding the light chain variable region of the monoclonal antibody.

Therein, the nucleotide sequence encoding the light chain variable region of the monoclonal antibody is shown in SEQ ID NOs: 30 to 34, or is a complementary sequence of SEQ ID NOs: 30 to 34.

In some specific embodiments of the present disclosure, the nucleotide has a nucleotide sequence that is obtained from the nucleotide sequence as shown in any one of SEQ ID NOs: 30 to 34 via substitution, deletion or addition of one or more nucleotides and has the same or similar function as the nucleotide sequence as shown in any one of SEQ ID NOs: 30 to 34.

In some specific embodiments of the present disclosure, for the nucleotide sequence that is obtained from the nucleotide sequence as shown in any one of SEQ ID NOs: 30 to 34 via substitution, deletion or addition of one or more nucleotides, the more nucleotides refer to 2, 3, 4 or 5 nucleotides.

The expression vector provided by the present disclosure comprises nucleotides encoding the anti-Aβ monoclonal antibody.

The present disclosure also provides a host cell that is transformed or transfected with the expression vector.

The preparation method of the anti-Aβ monoclonal antibody of the present disclosure comprises: culturing the host cell and inducing the expression of the anti-Aβ monoclonal antibody.

The present disclosure also provides a conjugate, comprising the monoclonal antibody that is chemically or biologically labeled.

The chemical label is an isotope, immunotoxin and/or chemical drug.

The biological label is a biotin, avidin or enzyme label.

The enzyme label is preferably horseradish peroxidase or alkaline phosphatase.

The immunotoxin is preferably aflatoxin, diphtheria toxin, *Pseudomonas aeruginosa* exotoxin, ricin, abrin, mistletoe lectin, volkensin toxin, PAP, saporin, gelonin or luffin.

The present disclosure also provides a coupling product that is prepared by coupling the monoclonal antibody or its conjugate with a solid medium or a semi-solid medium.

The solid medium or non-solid medium is selected from colloidal gold, polystyrene plates or beads.

The present disclosure also provides use of the monoclonal antibody, the conjugate and/or the coupling product in the manufacture of an agent for combating cognitive impairment, an agent for treating Alzheimer's disease, an agent for inhibiting the progression of Alzheimer's disease, an agent for inhibiting the formation of senile plaques, an agent for inhibiting Aβ accumulation, an agent for combating neurotoxicity, an agent for inhibiting the formation of Aβ amyloid fibrils, and/or an agent for combating synaptic toxicity.

The present disclosure also provides use of the humanized anti-Aβ monoclonal antibody, the conjugate and/or the coupling product in the manufacture of a medicament for the prevention and treatment of a disease;
the disease comprises amyloidosis, which is a disease and abnormality associated with amyloid protein, the amyloidosis comprises secondary amyloidosis and age-related amyloidosis, and the disease includes, but is not limited to, neurological disease such as Alzheimer's disease.

The present disclosure also provides a medicament, comprising the humanized anti-Aβ monoclonal antibody, its conjugate and/or coupling product.

The present disclosure also provides a method for the prevention and/or treatment of a disease, comprising administering the medicament of the present disclosure; the disease and disorder comprises amyloidosis, which is a disease and abnormality associated with amyloid protein, the amyloidosis comprises secondary amyloidosis and age-related amyloidosis, and the disease including but not limited to neurological disease such as Alzheimer's disease.

The humanized anti-Aβ monoclonal antibody provided by the present disclosure can inhibit the polymerization of Aβ monomers, protect nerve cells from the toxicity of Aβ, have a certain effect on improving cognitive learning and memory ability in Alzheimer's dementia model mice, and can be used for the treatment and diagnosis of a disease and disorder associated with amyloidosis, such as Alzheimer's disease.

The present disclosure also provides use of the humanized anti-Aβ monoclonal antibody, the conjugate and/or the coupling product in the manufacture of a product for detecting Aβ expression.

Experiments show that the humanized anti-Aβ monoclonal antibody provided by the present disclosure can bind to Aβ monomer. Therefore, the humanized anti-Aβ monoclonal antibody provided by the present disclosure can be used for the detection of Aβ monomer.

The present disclosure also provides a kit, comprising the humanized anti-Aβ monoclonal antibody, its conjugate and/or coupling product.

The kit for detecting Aβ monomer or polymer mixture provided by the present disclosure further comprises a coating buffer, a washing solution, a blocking solution and/or a color developing solution.

The coating buffer is a carbonate buffer.

The washing solution comprises PBS, Tween, sodium chloride, potassium chloride, disodium hydrogen phosphate, and dipotassium hydrogen phosphate.

The blocking solution comprises PBS and BSA.

The color developing solution comprises TMB solution, substrate buffer solution and stop solution.

The substrate buffer comprises citric acid and disodium hydrogen phosphate.

The stop solution is an aqueous hydrogen peroxide solution.

The kit for detecting a cell with surface expression of Aβ further comprises PBS, goat anti-mouse IgG Fc and TITC secondary antibody.

The present disclosure also provides a method for diagnosing a disease, comprising using the kit provided by the present disclosure to detect the expression of Aβ, and determining whether there is a disease based on the expression quantity of Aβ; the disease comprises amyloidosis, which is a disease and abnormality associated with amyloid protein, the amyloidosis comprises secondary amyloidosis and age-related amyloidosis, and the disease includes but is not limited to neurological disease such as Alzheimer's disease.

In some specific embodiments of the present disclosure, the standard for determining whether there is a disease based on the expression quantity of Aβ is: 600 to 1000 pg/ml for normal people, 200 to 450 pg/ml for AD patients, and the required detection sensitivity is <20 pg/ml.

Unless otherwise defined, all scientific and technological terms used herein have the same meaning as understood by those of ordinary skill in the art. For definitions and terms in this field, professionals can refer to Current Protocols in Molecular Biology (Ausubel). The abbreviation for amino acid residue is the standard 3-letter and/or 1-letter code used in the art for referring to one of the 20 commonly used L-amino acids.

"Antibody" refers to a protein composed of one or more polypeptides that can specifically bind to an antigen. One form of antibody constitutes the basic structural unit of an antibody. This form is a tetramer, which is composed of two pairs of identical antibody chains, each of which has a light chain and a heavy chain. In each pair of antibody chains, the variable regions of the light chain and the heavy chain are jointly responsible for binding the antigen, while the constant regions are responsible for the effector function of the antibody.

The "variable region" of an antibody heavy or light chain is a N-terminal mature region of the chain. Currently known antibody types include κ and λ light chains, as well as α, β (IgG1, IgG2, IgG3, IgG4), δ, ε, and μ heavy chains or their other type equivalents. The full-length immunoglobulin "light chain" (approximately 25 kDa or approximately 214 amino acids) comprises a variable region formed by approximately 110 amino acids at the $NH_2$-terminus, and a κ or λ constant region at the COOH-terminus. The full-length immunoglobulin "heavy chain" (approximately 50 kDa or approximately 446 amino acids) also comprises a variable region (approximately 116 amino acids) and one of the heavy chain constant regions, such as γ (approximately 330 amino acids).

"Antibody" comprises any isotype antibody or immunoglobulin, or antibody fragment that retains specific binding to the antigen, including but not limited to Fab, Fv, scFv and Fd fragments, chimeric antibodies, humanized antibodies, single chain antibodies, and fusion proteins comprising an antigen-binding portion of antibody and a non-antibody protein. The antibody can be labeled and detected. For example, it can be labeled and detected by radioisotopes, enzymes, fluorescent proteins, biotin and so on that can produce detectable substances. The antibody can also be bound to a solid carrier, including but not limited to polystyrene plates or beads.

"Humanized antibody" refers to an antibody that contains a CDR region derived from a non-human antibody, and other parts of the antibody molecule are derived from one (or several) human antibodies. Moreover, in order to retain binding affinity, some residues of the framework (referred to as FR) segment can be modified.

The "monoclonal antibody" refers to a preparation of antibody molecules with a single molecular composition. The monoclonal antibody composition shows a single binding specificity and affinity for a specific epitope.

The medicament comprises at least one functional ingredient, and further comprises a pharmaceutically acceptable carrier. Preferably, the pharmaceutically acceptable carrier is water, buffered aqueous solution, isotonic salt solution such as PBS (phosphate buffered saline), glucose, mannitol, dextrose, lactose, starch, magnesium stearate, cellulose, magnesium carbonate, 0.3% glycerin, hyaluronic acid, ethanol or polyalkylene glycols such as polypropylene glycol, triglycerides, etc. The type of pharmaceutically acceptable carrier used depends in particular on whether the composition according to the present disclosure is formulated for oral, nasal, intradermal, subcutaneous, intramuscular or intravenous administration. The composition according to the present disclosure may comprise a wetting agent, an emulsifier or a buffer substance as an additive.

As used herein, "CDR region" or "CDR" refers to a hypervariable region of the heavy chain and the light chain of immunoglobulin, as defined by Kabat et al. (Kabat et al., Sequences of proteins of immunological interest, 5th Ed., US Department of Health and Human Services, NIH, 1991, and later versions). There are three heavy chain CDRs and three light chain CDRs. Depending on the situation, the term CDR or CDRs as used herein is used to indicate one of these regions, or several or even all of these regions, which contain most of the amino acid residues responsible for binding by the affinity of the antibody to the antigen or its recognition epitope.

The present disclosure provides a method for antibody humanization modification, in which a reasonable antibody humanization design is carried out by referring to multi-template to perform FR transplantation, thereby obtaining a humanized antibody with an affinity equivalent to that of a murine antibody.

The preparation method of the humanized anti-Aβ monoclonal antibody provided by the present disclosure comprises:

Step 1: preparing mouse-derived hybridoma, obtaining an antibody sequence through 5'RACE;

Step 2: antibody humanization, in which sequence alignment is performed on the NCBI tool to complete the humanization modification, and the modified antibodies are screened.

Specifically, the method comprises as follows.

The method for preparing the humanized anti-Aβ monoclonal antibody comprises: using murine antibody 066-4.26.14 as a template, performing PCR amplification to obtain a heavy chain variable region gene VH and a light chain variable region gene VL of the antibody, and translating them into amino acid sequences, and then aligning the amino acid sequences with the human antibody sequences in the NCBI database, and selecting 5 human antibody sequences with the highest similarity to the VH and the VL of the variable regions as reference templates for the humanization modification, determining the CDR regions of the murine antibody 066-4.26.14, leaving the CDR regions unchanged, transplanting the FR regions from the 5 reference templates of the above VH and VL respectively to 066-4.26.14 to obtain humanized sequences, which are codon optimized and then separately subjected to the construction of expression vectors for transient transfection; transferring the expression vectors to 293E cells for expression to obtain humanized antibodies that specifically bind to Aβ; subjecting the humanized antibodies to affinity determination, antigen binding EC50 value determination, Aβ polymerization inhibition test and cytotoxicity protection test, and finally obtaining the humanized Aβ antibodies.

The humanized anti-Aβ monoclonal antibody provided by the present disclosure can inhibit the polymerization of Aβ monomers, protect nerve cells from the toxicity of Aβ, have a certain effect on improving the cognitive learning and memory ability in Alzheimer's dementia model mice, and can be used for the treatment and diagnosis of amyloidosis-associated diseases and disorders, such as Alzheimer's disease.

BRIEF DESCRIPTION OF THE DRAWINGS

In order to explain the examples of the present disclosure or the technical solutions in the prior art more clearly, the following will briefly describe the drawings that need to be used in the description of the examples or the prior art.

FIG. 1 shows the SDS-PAGE and WB detection results of Aβ monomer and polymer mixture; in which, lane M: protein molecular weight marker; lane 1: Aβ monomer; lane 2: Aβ polymer mixture; FIG. 1(A): SDS-PAGE detection results of Aβ monomer and polymer mixture; FIG. 1(B): WB detection results of Aβ monomer and polymer mixture;

FIG. 2 shows the SDS-PAGE detection results of the purified positive antibodies; in which, lane M: protein molecular weight marker; lane 1: 066-P01 (non-reducing); lane 2: 066-P01 (reducing); lane 3: 066-P02 (non-reducing); lane 4: 066-P02 (reducing); FIG. 2(A): SDS-PAGE detection results of the purified positive antibody 066-P01; FIG. 2(B): SDS-PAGE detection results of the purified positive antibody 066-P02;

FIG. 3 shows the detection results of anti-Aβ monoclonal antibodies in inhibiting Aβ polymerization; the abscissa represents different sample groups, the ordinate represents relative fluorescence intensity, and the anti-Aβ monoclonal antibodies such as 066-4.22.1, 066-4.26.14, 066-5.4.1 all can inhibit Aβ polymerization; in which, FIG. 3(A) shows the detection results of the sample groups IgG, anti-Aβ monoclonal antibodies 066-P01, 066-5.4.1, 066-6.1.1, 066-6.1.3, 066-6.2.1, 066-6.7.2 in inhibiting Aβ polymerization, respectively; FIG. 3(B) shows the detection results of the sample groups PBS, IgG, anti-Aβ monoclonal antibodies 066-4.21.13, 066-4.26.14, 066-4.6.8, 066-4.22.1, 066-4.18.2, 066-P01 in inhibiting Aβ polymerization, respectively;

FIG. 5 shows the protective activity detection results of anti-Aβ monoclonal antibodies against cytotoxicity; the abscissa represents different sample groups, the ordinate represents relative value of LDH release, the antibodies 066-4.26.14, 066-5.4.1, 066-6.1.1, 066-6.1.3, 066-6.2.1, 066-6.7.2, 066-7.17.2 all have protective effect against cytotoxicity, and their protective effect is equivalent to that of 066-P02; in which.

FIG. 7 shows the total RNA agarose gel electrophoresis detection results; in which lane M: DL2000 molecular weight marker; lane 1: total RNA of 066-4.26.14;

FIG. 8 shows the agarose gel electrophoresis detection results of the heavy chain variable region and light chain variable region PCR products of the candidate antibody; lane M: DL2000 molecular weight marker; lane 1: PCR product of 066-4.26.14 heavy chain variable region; lane 2: PCR product of 066-4.26.14 light chain variable region; in which, FIG. 8(A) shows the PCR results of 066-4.26.14 heavy chain variable region; FIG. 8(B) shows the PCR results of 066-4.26.14 light chain variable region;

FIG. 9 shows the SDS-PAGE detection results of the purified mouse-human chimeric antibody 066-4.26.14-chAb; lane M: protein molecular weight marker; lane 1: mouse-human chimeric antibody 066-4.26.14-chAb (non-reducing); lane 2: mouse-human chimeric antibody 066-4.26.14-chAb (reducing); FIG. 9(A) shows the non-reducing electrophoresis results of mouse-human chimeric antibody 066-4.26.14-chAb; FIG. 9(B) shows the reducing electrophoresis results of mouse-human chimeric antibody 066-4.26.14-chAb;

FIG. 10 shows the SDS-PAGE detection results of the purified humanized candidate antibodies; lane M: protein molecular weight marker.

SPECIFIC MODELS FOR CARRYING OUT THE PRESENT DISCLOSURE

Figure 4:
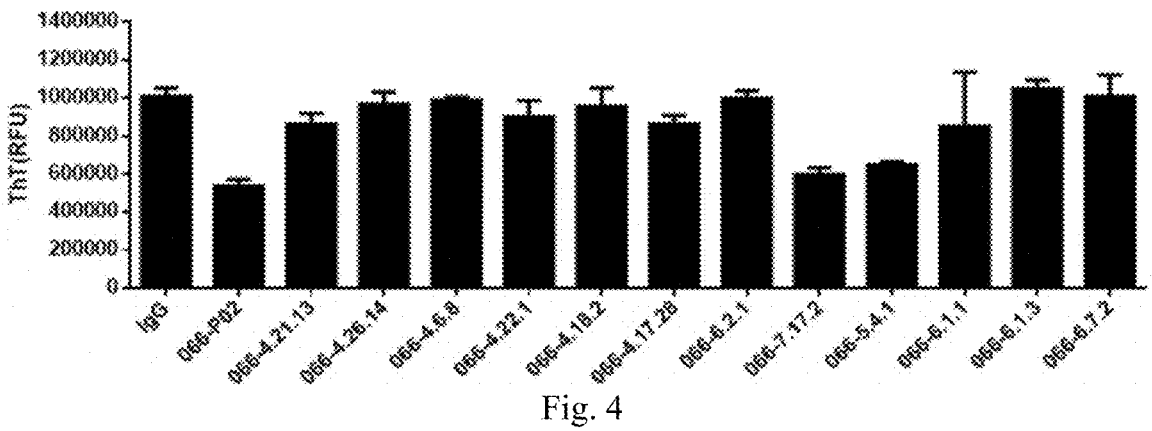
FIG. 4 shows the activity detection results of anti-Aβ monoclonal antibodies in promoting macrophage phagocytosis of Aβ; the abscissa represents different sample groups, the ordinate represents fluorescence intensity, and the anti-Aβ monoclonal antibodies 066-5.4.1, 066-7.17.2 have the activities of promoting macrophages phagocytosis of Aβ.

The present disclosure discloses a humanized anti-Aβ monoclonal antibody and use thereof, and those skilled in the art can fulfill them by learning the contents of the present disclosure and appropriately improving the process parameters. In particular, it should be pointed out that all similar substitutions and modifications are obvious to those skilled in the art, and they are all deemed to be included in the present disclosure. The methods and use of the present disclosure have been described through the preferred examples, and it is obvious that those skilled in the art can make changes or appropriate alternations and combinations to the methods and use described herein without departing from the content, spirit and scope of the present disclosure, so as to achieve and apply the technology of the present disclosure.

The humanized anti-Aβ monoclonal antibodies provided by the present disclosure and the raw materials and reagents used in the use were all commercially available.

The present disclosure is further illustrated in conjunction with the following examples:

Example 1: Preparation of Aβ Antigen and Positive Control Antibody

Preparation of Aβ Monomer and Polymer Mixture $Aβ_{1-42}$, $Aβ_{1-16}$, and $Aβ_{14-29}$ polypeptides were synthesized by Ji'er Biochemical (Shanghai) Co., Ltd.

The amino acid sequence of $Aβ_{1-42}$ polypeptide was:
(SEQ ID: 35)
DAEFRHDSGYEVHHQKLVFFAEDVGSNKGAIIGLMVGGVVIA, the amino acid sequence of $Aβ_{1-16}$ polypeptide was:
(SEQ ID: 36)
DAEFRHDSGYEVHHQK,
and the amino acid sequence of $Aβ_{14-29}$ polypeptide was:
(SEQ ID: 37)
HQKLVFFAEDVGSNKGA.

Preparation method of $Aβ_{1-42}$ monomer (abbreviated as Aβ monomer): 1 ml of hexafluoro isopropanol (HFIP) was added to 1 mg of $Aβ_{1-42}$ polypeptide dry powder, subjected to vortex and shaking for 1 min, and sonicated in a water bath for 1-5 min until the dissolution was completed; placed in 37° C., 200 rpm shaking incubator and shaken for 1.5 hours; a vacuum rotary dryer was used to volatilize hexafluoro isopropanol; 192 µl of anhydrous dimethyl sulfoxide (DMSO) was added to the dried $Aβ_{1-42}$ polypeptide to dissolve the polypeptide, then added with 27 µl of 20×PBS solution, 54 µl of 2% SDS, 267 µl of ddH$_2$O, mixed well, subpackaged in small amounts, stored in a refrigerator at −80° C., which was the $Aβ_{1-42}$ monomer; and the detection thereof was performed by SDS-PAGE and WB (hybridization detection was performed by using the positive antibody 066-P02 that specifically recognizes $Aβ_{1-42}$) (see FIG. 1).

Preparation method of $Aβ_{1-42}$ polymer mixture (abbreviated as Aβ polymer mixture): 1 ml of hexafluoro isopropanol (HFIP) was added to 1 mg of $Aβ_{1-42}$ polypeptide dry powder, subjected to vortex and shaking for 1 min, sonicated in a water bath for 1-5 min until the dissolution was completed; placed in 37° C., 200 rpm shaking incubator and shaken for 1.5 h; a vacuum rotary dryer was used to volatilize hexafluoro isopropanol; 192 µl of DMSO was added to the dry $Aβ_{1-42}$ polypeptide to dissolve the polypeptide, then added with 27 µl of 20×PBS solution, 54 µl of 2% SDS, 267 µl of ddH$_2$O, mixed well, and placed in a 37° C. water bath for 18-24 h; added with 1.62 ml of ddH$_2$O, mixed well, and placed in a 37° C. water bath for 18-24 h; transferred into PBS by using 10 KDa ultrafiltration tube for buffer replacement, subpackaged in small amounts, stored in a refrigerator at −80° C., which was the $Aβ_{1-42}$ polymer mixture; and the detection thereof was performed by SDS-PAGE and WB (hybridization detection was performed using the positive antibody 066-P02 that specifically recognizes $Aβ_{1-42}$) (see FIG. 1).

2. Construction of Positive Control Antibody Expression Vector pGS003-hIgG1CH and pGS003-hIgKCL were separately selected as the expression vectors for constructing the heavy chain and the light chain of anti-human Aβ-positive antibodies (066-P01: Solanezumab, Eli lily; 066-P02: Aducanumab, Biogen); after the codon optimization of the amino acid sequences of the positive antibody variable regions, the positive antibody VH and VL genes were separately cloned into pGS003-hIgG1CH and pGS003-hIgKCL using restriction enzyme digestion method to obtain transient transfection expression vectors pGS003-066-P01VH-hIgG1CH, pGS003-066-P01VL-hIgKCL, pGS003-066-P02VH-hIgG1CH and pGS003-066-P02VL-hIgKCL of the heavy chain and the light chain of the positive antibody. The amino acid sequence of the heavy chain variable region of the positive antibody 066-P01 was as follows (SEQ ID: 38):

EVQLVESGGGLVQPGGSLRLSCAASGFTFSRYSMSWVRQAPGKGLELVAQ

INSVGNSTYYPDTVKGRFTISRDNAKNTLYLQMNSLRAEDTAVYYCASGD

YWGQGTLVTVSS

The amino acid sequence of the light chain variable region of the positive antibody 066-P01 was as follows (SEQ ID: 39):

DVVMTQSPLSLPVTLGQPASISCRSSQSLIYSDGNAYLHWFLQKPGQSPR

LLIYKVSNRFSGVPDRFSGSGSGTDFTLKISRVEAEDVGVYYCSQSTHVP

WTFGQGTKVEIK

The amino acid sequence of the heavy chain variable region of the positive antibody 066-P02 was as follows (SEQ ID: 40):

QVQLVESGGGVVQPGRSLRLSCAASGFAFSSYGMHWVRQAPGKGLEWVAV

IWFDGTKKYYTDSVKGRFTISRDNSKNTLYLQMNTLRAEDTAVYYCARDR

GIGARRGPYYMDVWGKGTTVTVSS

The amino acid sequence of the light chain variable region of the positive antibody 066-P02 was as follows (SEQ ID: 41):

DIQMTQSPSSLSASVGDRVTITCRASQSISSYLNWYQQKPGKAPKLLIYA

ASSLQSGVPSRFSGSGSGTDFTLTISSLQPEDFATYYCQQSYSTPLTFGG

GTKVEIK

3. Expression by Transient Transfection pGS003-066-P01VH-hIgG1CH and pGS003-066-P01VL-hIgKCL;

pGS003-066-P02VH-hIgG1CH and pGS003-066-P02VL-hIgKCL were transiently expressed.

FreeStyle™ 293E cells were used for expression by transient transfection in Freestyle medium. Twenty-four hours before transfection, 30 ml of 293E cells were inoculated at $0.5 \times 10^6$ cells/ml in a 125 ml conical flask, and cultured on a shaker at 130 rpm in a 37° C., 5% $CO_2$ incubator. During transfection, 60 µl of 293E Fectin was firstly taken and added to 1 ml of Opti-MEM, mixed well, and incubated at room temperature for 5 minutes; meanwhile, Total 30 µg plasmid DNA of transient transfection expression vectors (recombinant vectors) was dissolved in 1 ml of Opti-MEM. Then, the plasmid DNA and 293E Fectin were mixed thoroughly, with a total volume of 2 ml, incubated at room temperature for 15 minutes, and then all the mixture was added to the cell culture wells, mixed, and incubated on a shaker in a 37° C., 5% $CO_2$ incubator at 130 rpm for 7 days. The culture broth was centrifuged at a high speed and the supernatant was taken and subjected to vacuum filtration with a microporous membrane.

4. Purification of Protein

According to the operating method provided by the manufacturer, Protein A column (protein purification liquid chromatography system/AKTA Purifier 10, GE) and nickel column were used for purification to obtain purified positive antibodies 066-P01 and 066-P02. As shown in FIG. 2.

Example 2: Preparation of Anti-Aβ Monoclonal Hybridoma

Immunization of BALB/c Mice $A\beta_{1-42}$ polypeptide antigen and Freund's complete adjuvant were vortexed and mixed according to their doses, after emulsification was completed, first immunization was performed to 6-week-old BALB/c female mice. Each mouse was injected intraperitoneally with 200 µg of antigen, in total 3 groups of mice were immunized, 5 mice in each group. Two weeks after the first immunization, the mice were given second intraperitoneal immunization, in which Freund's incomplete adjuvant was used, while the dose of immune antigen was the same as the first immunization. After that, the mice were immunized intraperitoneally twice a month, and the adjuvant and antigen doses were the same as the second immunization.

After the first immunization, a small amount of blood was collected from mouse orbit and serum titer was tested every six weeks. After the serum titer reached 1:200000 or above by the indirect ELISA method, the mice used for fusion were subjected to booster immunization.

Preparation of Myeloma Cells for Fusion

Myeloma cells P3X63Ag8.653 used for fusion were resuscitated three weeks in advance, cultured in DMEM medium containing 1×8-azaguanine and 10% fetal bovine serum for two weeks, and cultured with DMEM containing 10% fetal bovine serum before one week of fusion, in which the density of P3X63Ag8.653 was maintained at 70% to 80% until the day of fusion.

Cell Fusion and HA Screening

Obtaining and preparation of spleen cells: 2 mice after booster immunization were taken, sacrificed after collection of immune serum, and soaked in 75% alcohol for 2-3 minutes. The skin and peritoneum on the abdomen side of the immunized mice were cut to expose spleen. The spleen was obtained by removing the surrounding tissues with scissor tip, ground with a grinding rod, and filtered through a cell sieve to prepare a single cell suspension. The supernatant was discarded after centrifugation.

Treatment before cell fusion: P3X63Ag8.653 in the culture flask was collected, centrifuged at 1000 rpm/5 min, then the supernatant was discarded, the cells were resuspended, and the live myeloma cells were counted. The spleen cell suspension was centrifuged to discard the supernatant, added with ACK lysate, incubated and centrifuged to discard supernatant to remove red blood cells, resuspended in DMED, and the viable spleen cells were counted.

Cell fusion: The cells were mixed at the ratio of spleen cells:P3X63Ag8.653=1:2, centrifuged at 2000 rpm/5 min to discard the supernatant, shaken to disperse cell pellets, added with 1 mg/ml Pronase at 400 µl/$1 \times 10^8$ spleen cells; after incubating for 15 seconds, 10 ml of fetal bovine serum was added to stop the reaction, electroporation solution (ECF) was supplemented to 50 ml, centrifuged at 2500 rpm for 5 minutes to discard the supernatant, resuspended with ECF and the viable cells were counted, and the spleen cell density was adjusted to $2 \times 10^6$/ml. The cell suspension with the well-adjusted density was added to an electrofusion tank, and an electroporator was run for cell fusion. After the fusion, the cell suspension was transferred from the fusion tank to ½ HA medium, allowed to stand for 3 hours and then cell plating was carried out.

HA medium selection: AT selection medium containing ½ HA, 1×penicillin-streptomycin, 20% fetal bovine serum and 80% DMEM medium was prepared. The mouse hybridoma cells were resuspended in the above ½ HA selection medium and mixed well. The cell suspension was added to a 96-well cell culture plate at 200 µl/well, $1 \times 10^6$ spleen cells/plate, placed in a cell incubator and cultured at 37° C. After 1 week of culture, the ½ HA medium was used for the first renewing of the medium, and the culture was continued in 37° C. cell incubator. After 3 days of culture, the ½ HA medium was used for the second renewing of the medium.

Screening of Positive Cell Lines

Two weeks after the fusion, the cell supernatant was taken and subject to ELISA experiment to detect the binding of the cell supernatant to human $A\beta_{1-42}$, and after the cells with positive ELISA result were screened out, the second ELISA experiment was retested. The cell supernatant with positive retested results was taken for subcloning and expansion culture.

Expansion Culture

The cell lines with positive ELISA test result were transferred from the 96 well-plate to a 24 well-plate and cultured, after the cells grew all over the plate, and they were transferred to a 25 cm² culture flask and cultured.

Subcloning by Limiting Dilution Method

The positive cell lines were mixed well by beating and pipetting, and a small amount thereof was pipetted to count the viable cells. About 200 cells were pipetted and added to 80 ml of complete medium and mixed well, and plated on 4 plates. In addition, about 400 cells were pipetted and added to 80 ml of complete medium and mixed well, and plated on 4 plates. In addition, about 1000 cells were pipetted and added to 20 ml of complete medium and mixed well, and plated on 1 plate. A total of 9 plates were plated at 3 different cell densities, respectively 0.5 cells/well, 1 cell/well, and 10 cells/well. The 96-well plates were plated in a 37° C., 5% $CO_2$ incubator for culture.

Clone Detection and Expansion Culture

The supernatants of the monoclonal cell wells were taken for ELISA to detect the binding of the cloned antibody to the full length of $A\beta_{1-42}$ as well as the N-terminal, C-terminal and middle peptide fragments of $A\beta_{1-42}$, respectively.

Coating: Streptavidin was diluted with CBS (pH 9.6) to 1 µg/ml, added to 96-well microtiter plate, 50 µl per well, incubated overnight at 2-8° C.

Blocking: After washing the plate once with PBST, it was blocked with 1% BSA, 200 µl per well, and incubated for 1 hour at room temperature.

Antigen: After washing the plate three times with PBST, the biotinylated $A\beta_{1-42}$, $A\beta_{1-16}$, and $A\beta_{14-29}$ polypeptides were taken respectively, diluted with PBS (pH 7.2) to 1 µg/ml, and added to enzyme-labeled 96 well-plate, 50 µl per well, and incubated for 1 hour at room temperature.

Addition of primary antibody: After washing the plate three times with PBST, mouse candidate antibody was added, 50 µl/well, and incubated at room temperature for 2 hours.

Addition of secondary antibody: After washing the plate three times with PBST, anti-mouse IgG Fc-HRP antibody in 1:5000 diluent was added, 50 µl/well, and incubated for 1 hour at room temperature.

Color development: After washing the plate six times with PBST, TMB color development solution was added, 50 µl per well, and developed in the dark for 10 minutes at room temperature.

Stop: a stop solution was directly added to stop the reaction, 50 µl per well.

Detection: After stopping the reaction, the microtiter plate was immediately placed into a microplate reader, the OD value was measured at 450 nm, and the original data was stored.

Data processing: The raw data were input into the software SoftMax Pro 6.2.1 for data processing. See Table 1 for specific data. The results showed that the 12 murine candidate antibodies contained three different antigen binding epitopes, namely N-terminal ($A\beta_{1-16}$), C-terminal ($A\beta_{30-42}$), and middle ($A\beta_{14-29}$) peptide fragments, in which, the antigen binding epitope of 066-4.26.14 was grouped into $A\beta_{1-42}$ C-terminal peptide fragment (because 066-4.26.14 could bind to the full length of $A\beta_{1-42}$, but did not bind to $A\beta_{1-16}$, $A\beta_{14-29}$, it was deduced that it bound to $A\beta_{30-42}$ region).

The cell lines with positive ELISA result were transferred from the 96 well-plate to a 24 well-plate for culture, and the cells grew over the plate, they were transferred to a 25 cm² culture flask and cultured.

TABLE 1

Grouping detection results of murine candidate antibody antigen binding epitopes

| Antibody name | Full length $A\beta_{1-42}$ | $A\beta_{1-16}$ (N-terminal peptide fragment) | $A\beta_{14-29}$ (middle peptide fragment) | Epitope |
|---|---|---|---|---|
| 066-4.6.8 | 1.2944 | 0.0561 | 0.5115 | Middle peptide fragment |
| 066-4.17.28 | 1.4540 | 0.0690 | 1.1238 | Middle peptide fragment |
| 066-4.18.2 | 1.0925 | 1.2210 | 0.0848 | N-terminal peptide fragment |
| 066-4.21.13 | 1.3647 | 0.056 | 1.1457 | Middle peptide fragment |
| 066-4.22.1 | 1.2517 | 0.0773 | 1.0401 | Middle peptide fragment |
| 066-4.26.14 | 1.9312 | 0.0602 | 0.0674 | C-terminal peptide fragment |
| 066-5.4.1 | 1.2483 | 0.0540 | 1.1566 | Middle peptide fragment |
| 066-6.1.1 | 1.3752 | 0.1001 | 0.1180 | C-terminal peptide fragment |
| 066-6.1.3 | 1.3665 | 0.0618 | 0.0803 | C-terminal peptide fragment |
| 066-6.2.1 | 1.3085 | 0.0975 | 0.1003 | C-terminal peptide fragment |
| 066-6.7.2 | 1.4707 | 1.6608 | 0.3058 | N-terminal peptide fragment |
| 066-7.17.2 | 1.0833 | 0.9197 | 0.0612 | N-terminal peptide fragment |

Identification of Subtypes

Goat anti-mouse IgG1, IgG2a, IgG2b, IgG2c, IgG3, IgM and IgA were coated, 50 ng/100 µl/well, 4° C. overnight, blocked with BSA at room temperature, the cell supernatant to be tested was added, incubated at room temperature for 2 hours, added with enzyme-labeled secondary antibody goat anti-mouse IgG, κ, λ, after color development, stopping, and 450 nm reading, it was judged that the tested cell line was subtypes IgG1, κ or IgG2a, κ or IgG2b, κ. The results are shown in Table 2, in which for the antibody 066-4.26.14, its heavy chain constant region was murine IgG2a, and its light chain constant region was the constant region of the murine κ chain.

TABLE 2

Detection results of mouse candidate subtypes

| Antibody name | Subtype |
|---|---|
| 066-4.6.8 | IgG1, Kappa |
| 066-4.17.28 | IgG1, Kappa |
| 066-4.18.2 | IgG2b, Kappa |
| 066-4.21.13 | IgG1, Kappa |
| 066-4.22.1 | IgG1, Kappa |
| 066-4.26.14 | IgG2a, Kappa |
| 066-5.4.1 | IgG1, Kappa |
| 066-6.1.1 | IgG2a, Kappa |
| 066-6.1.3 | IgG2a, Kappa |
| 066-6.2.1 | IgG2a, Kappa |
| 066-6.7.2 | IgG2a, Kappa |
| 066-7.17.2 | IgG1, Kappa |

Cell Cryopreservation

Preparation of cryopreservation solution: 90% fetal bovine serum, 10% DMSO.

The cells in the culture flask were resuspended; after the cell counting, the cells were centrifuged at 1000 rpm/min for 5 min, the supernatant was discarded, and the suspension was beaten by pipetting with fetal bovine serum containing 10% DMSO, stored at $5\times10^6$ cells/tube in a cryopreservation box at −80° C. overnight, and transferred into liquid nitrogen on the next day.

Preservation of Monoclonal Hybridoma Gene

Positive monoclonal cell lines were collected, added with TRizol to lyse the cells and extract RNA, which was reverse-transcribed into cDNA, and stored at −80° C.

Preparation of Antibodies by in Vitro Culture Method

The prepared hybridoma cell lines were resuscitated by a method as follows. The hybridoma cell lines were resuscitated in a DMEM medium containing 10% fetal bovine serum and 1% penicillin streptomycin, and cultured in a vial; after the cell confluence was about 90%, passage expansion was performed, the expansion was performed until the cell culture supernatant in total was about 200 ml, then the supernatant was collected, centrifuged and filtered for purification.

Example 3: Detection of Anti-Aβ Monoclonal Antibody in Inhibiting Aβ Polymerization 8.2% DMSO/DPBS solution (DMSO: sigma; DPBS: Hyclone) was used to dissolve Aβ dry powder to 1 mg/ml, the Aβ solution was diluted with DPBS to 33 μg/ml, the anti-Aβ monoclonal antibodies 066-4.6.8, 066-4.18.2, 066-4.22.1, 066-4.26.14, 066-5.4.1, 066-6.1.1, 066-6.1.3, 066-6.2.1, 066-6.7.2 were diluted to 450 μg/ml (IC100), and ThT (sigma) was diluted with ultrapure water to 20 μM. 50 μl of antibody diluent was taken and added to a 96-well black plate (corning), then added with 50 μl of Aβ diluent, finally added with 100 μl of ThT, incubated for 24 hours at room temperature in the dark, and the fluorescence intensity (Ex/Em=440/485) was detected with a multifunctional microplate reader. The abscissa represented different sample groups, and the ordinate represented relative fluorescence intensity. The results are shown in FIG. 3. In FIG. 3(A), when the relative fluorescence intensity of the IgG group was 1.0, the relative fluorescence intensity of the anti-Aβ monoclonal antibody 066-5.4.1 group was 0.59; in FIG. 3(B), when the relative fluorescence intensity of the PBS group was 1.0, the relative fluorescence intensity of the anti-Aβ monoclonal antibody 066-4.22.1 group was 0.44, and the relative fluorescence intensity of the anti-Aβ monoclonal antibody 066-4.26.14 group was 0.46; it could be seen that the anti-Aβ monoclonal antibodies such as 066-4.22.1, 066-4.26.14 and 066-5.4.1 all could inhibit Aβ polymerization.

Example 4: Detection of Activity of Anti-Aβ Monoclonal Antibody in Promoting Macrophage Phagocytosis of Aβ

Mouse primary peritoneal macrophages that were in good condition after 3 days of adherent culture were digested with 0.25% trypsin and counted. The cell density was adjusted to $2 \times 10^5$/ml with DMEM medium (Gibco) containing 10% fetal bovine serum and the cells were inoculated on a 96-well cell culture plate, 100 μl/well; the anti-Aβ monoclonal antibodies 066-4.6.8, 066-4.17.28, 066-4.18.2, 066-4.21.13, 066-4.22.1, 066-4.26.14, 066-5.4.1, 066-6.1.1, 066-6.1.3, 066-6.2.1, 066-6.7.2, 066-7.17.2 were diluted with DMEM medium containing 1% fetal bovine serum to 20 μg/ml and used as working solutions, Aβ was diluted to 240 μg/ml, and ThT (sigma) was diluted to 20 μM with ultrapure water. The culture medium in the culture plate was discarded, 50 μl of antibody diluent was first added, then added with 50 μl of Aβ diluent, multiple wells were set; incubation was performed in a 37° C., 5% $CO_2$ incubator for 6 hours; 50 μl of supernatant was taken and add to a 96-well black plate, then added with 50 μl of ThT, and the fluorescence intensity (Ex/Em=440/485) was detected with a multifunctional microplate reader. The abscissa represented different sample groups, and the ordinate represented fluorescence intensity. The results are shown in FIG. 4. Among them, the fluorescence intensity of the anti-Aβ monoclonal antibody 066-5.4.1 group was 650,000, and the fluorescence intensity of the anti-Aβ monoclonal antibody 066-7.17.2 group was 600,000. It could be seen that the anti-Aβ monoclonal antibodies 066-5.4.1, 066-7.17.2 had the activity of promoting the phagocytosis of Aβ by macrophages.

Figure 5A:
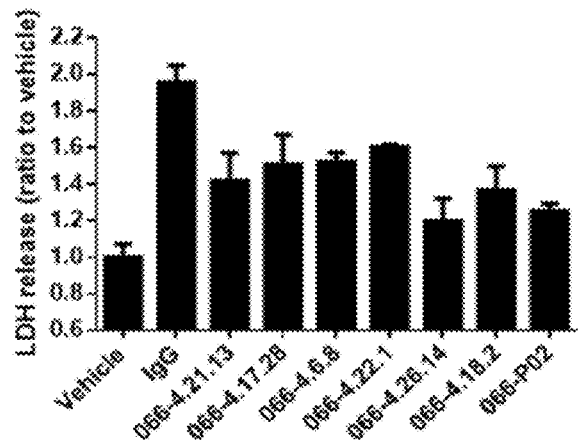
FIG. 5(A) shows the protective activity detection results of sample groups Vehicle, IgG, anti-Aβ monoclonal antibodies 066-4.21.13, 066-4.17.28, 066-4.6.8, 066-4.22.1, 066-4.26.14, 066-4.18.2, 066-P02 against cytotoxicity, respectively.
Figure 5B:
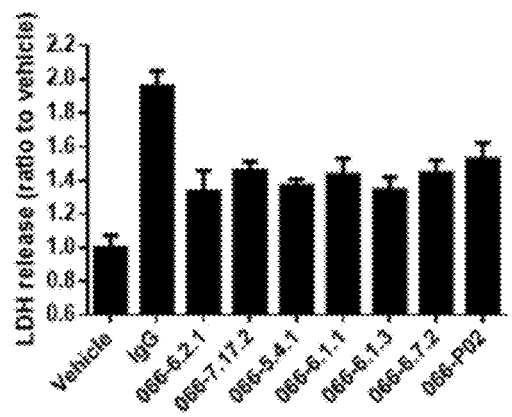
FIG. 5(B) shows the protective activity detection results of sample groups Vehicle, IgG, anti-Aβ monoclonal antibodies 066-6.2.1, 066-7.17.2, 066-5.4.1, 066-6.1.1, 066-6.1.3, 066-6.7.2, 066-P02 against cytotoxicity, respectively.

Example 5: Detection of Protective Activity of Anti-Aβ Monoclonal Antibody Against Cytotoxicity Logarithmic growth phase SHSY5Y cells were digested with 0.25% trypsin, counted, adjusted with EMEM medium (ATCC) containing 10% fetal calf serum to a cell density of $3 \times 10^4$/ml, inoculated on a 96-well cell culture plate, 100 μl/well; the anti-Aβ monoclonal antibodies 066-4.6.8, 066-4.17.28, 066-4.18.2, 066-4.21.13, 066-4.22.1, 066-4.26.14, 066-5.4.1, 066-6.1.1, 066-6.1.3, 066-6.2.1, 066-6.7.2, 066-7.17.2 were diluted with EMEM medium containing 1% fetal bovine serum to 200 μg/ml (IC100), and used as working solution, Aβ was diluted to 240 μg/ml. The culture medium in the culture plate was discarded, 50 μl of antibody diluent was added, then added with 50 μl of AP diluent, multiple wells were set; incubation was performed in a 37° C., 5% $CO_2$ incubator for 48 hours; 50 μl of the supernatant was taken and added to a new 96 well-plate, then added with 50 μl of LDH assay buffer, reacted in the dark at room temperature for 30 minutes, added with 50 μl of stop solution, and the absorbance value was measured with a multifunctional microplate reader. The abscissa represented different sample groups, and the ordinate represented relative value of LDH release. The results are shown in FIG. 5. Among them, when the relative value of LDH release of the Vehicle group was 1.0, the relative fluorescence intensity of the anti-Aβ monoclonal antibody 066-4.26.14 group was 1.2, the relative value of LDH release of the anti-Aβ monoclonal antibody 066-5.4.1 group was 1.37, the relative value of LDH release of the anti-Aβ monoclonal antibody 066-6.1.1 group was 1.43, the relative value of LDH release of the anti-Aβ monoclonal antibody 066-6.1.3 group was 1.35, the relative value of LDH release of the anti-Aβ monoclonal antibody 066-6.2.1 group was 1.34, the relative value of LDH release of the anti-Aβ monoclonal antibody 066-6.7.2 group was 1.44, the relative value of LDH release of the positive control antibody 066-P02 group was 1.26 (A) and 1.53 (B). It could be seen that the antibodies 066-4.26.14, 066-5.4.1, 066-6.1.1, 066-6.1.3, 066-6.2.1, 066-6.7.2, 066-7.17.2 all had protective effect against cytotoxicity, and the protective effect was equivalent to that of 066-P02.

Example 6: Morris Water Maze Experiment

1. Experimental Method and Steps:
    Experimental animals 3×Tg mice were purchased from Beijing Weitong Lihua Experimental Animal Technology Co., Ltd. and raised by the Experimental Animal Center of Medical College of Jilin University. The grouping situation was as follows:
        according to the different drugs to be injected, they were divided into antibody 066-4.26.14 treatment group, antibody 066-5.4.1 treatment group, antibody 066-7.17.2 treatment group, 3×Tg blank control group, wild-type PBS injection group, positive antibody 066-P02 control group, 8 animals in each group.
    By referring to the literature method (Nabeshima, 2007), 6-month-old male 3×Tg mice (500 g/mouse) were intraperitoneally injected with monoclonal antibodies 066-4.26.14, 066-5.4.1, 066-7.17.2, once per week, continuously injected for 10 weeks, and Morris water maze test was performed 8 weeks after injection.
Morris Water Maze Test Steps:
    (1) The specially designed water maze was mainly composed of a cylindrical pool and a movable platform. The pool had a height of 45 cm and a diameter of 100 cm, the platform had a diameter of 9 cm and an adjustable height from 15 to 40 cm, and digital camera was mounted above the pool and connected to a computer.
(2) Clean water was filled into the pool in advance. The walls and bottom of the pool were all black. White pigment for food was added to the pool water to prevent mice from seeing the platform under the water surface. The water depth was 30 cm and the water surface was 1 cm higher than the platform.
(3) The water temperature was controlled at 19±1° C., and except the quadrant where the platform was located, other quadrants on the pool were marked with points for entering water. On the sidewalls corresponding to each quadrant, markers of different shapes were adhered. The position of the platform was unchanged during the experiment.
(4) Each test was carried out in a soundproof room, and the positions of laboratory objects such as the pool, light sources, and cages remained unchanged.
(5) In the $8^{th}$ week, training was started on the $3^{rd}$ day after the administration. The experiment lasted for 5 days (water maze-hidden platform test), 4 times a day. When the mouse entered the water, it faced the wall of the pool and was gently put into the water. Five training sessions (experiments) a day were conducted randomly in areas other than the quadrant where the platform was located, and the first two training sessions in the first two days of the experiment were performed as exercises. If the mouse found the platform within 60 seconds, it was allowed to stay on the platform for 15 seconds. If the mouse could not find the platform within 60 seconds (the latent period was recorded as 60 seconds), the experimenter would guide it to the platform and stay on the platform for 15 seconds. The average of four latent periods of the mouse was taken as the daily performance of the mouse.

Figure 6:
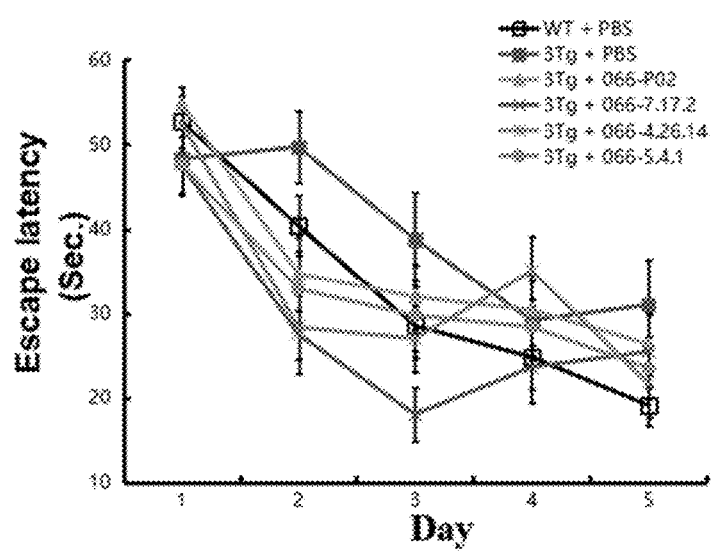
FIG. 6 shows the detection results of the Morris water maze experiment; in which the abscissa represents time after treatment (Days 1, 2, 3, 4 and 5), and the ordinate represents time to find hidden platform under water surface (unit: Sec)

2. Experimental Results (see FIG. 6):

On the second day of Hidden platform test, the time to find the hidden platform under the water (escape latent period) was significantly shortened for all antibody administration groups compared with the 3×Tg blank group, which was statistically significant. On day 3, the anti-Aβ monoclonal antibody 066-7.17.2 group took 18 s for escape latent period, the anti-Aβ monoclonal antibody 066-4.26.14 group took 27 s for escape latent period, the anti-Aβ monoclonal antibody 066-5.4.1 group took 30 s for escape latent period, and the blank control group took 39 s for escape latent period, in which the 066-7.17.2 and 066-4.26.14 administration groups had a significantly shorter escape latent period as compared with the 3×Tg blank group, and there was statistical significance. It could be seen that the anti-Aβ monoclonal antibodies 066-7.17.2 and 066-4.26.14 had a certain effect on improving the cognitive learning and memory ability in Alzheimer's dementia model mice.

Example 7: Monoclonal Antibody Gene Sequencing and Chimeric Antibody Preparation 1. Monoclonal Antibody Gene Sequencing After immunization, fusion and monoclonalization, based on the experimental results of binding epitope, detection of inhibiting Aβ polymerization, detection of protective activity against cytotoxicity, Morris water maze, etc., the 066-4.26.14 monoclonal antibody cell line was selected for total RNA extraction which was reverse-transcribed into cDNA, and then the cDNA was used as a template for PCR amplification of the heavy chain variable region and light chain variable region of the antibody.

The TRIzol reagent kit (15596-026) of Invitrogen was used, and the total RNA was extracted from the 066-4.26.14 monoclonal antibody cell line according to its instructions. The results are shown in FIG. 7.

The 5'RACE FULL kit (D315) of Takara was then used, the total RNA was reverse-transcribed into the first strand cDNA using the random primers in the kit, and then the PCR amplification of heavy chain was performed using the constant region primer mIgGR (5'-CTCAGGGAAR-TARCCYTTGAC-3', SEQ ID NO: 42) and the RACE primer in the kit, and the PCR amplification of light chain was performed using the constant region primer mIgKR (5'-TCACTGCCATCAATCTTCCAC-3', SEQ ID NO: 43) and the RACE primer in the kit. The results are shown in FIG. 8.

The PCR fragments were recovered by the agarose gel recovery kit and subjected to TA cloning, and then single clones were picked up for colony PCR. The colony PCR primers were M13F (5'-TGTAAAACGACGGCCAGT-3', SEQ ID NO: 44) and M13R (5'-CAGGAAACAGC-TATGACC-3', SEQ ID NO: 45). Part of the samples selected from the correct strains upon the identification were sent to Invitrogen for sequencing. It was finally determined that the nucleotide sequence of the heavy chain variable region was SEQ ID NO: 46, the nucleotide sequence of the light chain variable region was SEQ ID NO: 47, the amino acid sequence of the heavy chain variable region was SEQ ID NO: 48, and the amino acid sequence of the light chain variable region was SEQ ID NO: 49, see Table 3.

TABLE 3

Specific sequences of heavy chain variable region and light chain variable region of 066-4.26.14 antibody

| | Nucleotide sequence | | Amino acid sequence | |
| --- | --- | --- | --- | --- |
| Antibody | Heavy chain variable region | Light chain variable region | Heavy chain variable region | Light chain variable region |
| 066-4.26.14 | SEQ ID NO: 46 | SEQ ID NO: 47 | SEQ ID NO: 48 | SEQ ID NO: 49 |

The nucleotide sequence of the heavy chain variable region of the 066-4.26.14 antibody was as follows (SEQ ID NO: 46):

```
GAAGTGAAGCTGGTGGAGTCTGGGGGAGGCTTAGTGAAGCCTGGAGGGTC

CCTGAAACTCTCCTGTGCAGCCTCTGGATTCACTTTCAGAAGTTATGCCA

TGTCTTGGGTTCGCCAGACTCCAGAGAAGAGGCTGGAGTGGGTCGCATCC

ATTAGTACTACTAGTAACACCTACTATCCAGACAGTGTGAAGGGCCGATT

CACCACCTCCAGAGATAACGCCAGGAACATCGTGTACCTGCAAATGAGCA

GTCTGAGGTCTGACGACACGGCCATGTATTACTGTGGAAGAGGCGTGATT

ACGAACCAGGCCTGGTTTGCTTACTGGGGCCAAGGGACTCTGGTCACTGT

CTCTGCA
```

The nucleotide sequence of the light chain variable region of the 066-4.26.14 antibody was as follows (SEQ ID NO: 47):

GATATTGTGCTAACTCAGTCTCCAGCCACCCTGTCTGTGACTCCAGGAGA

TAGCGTCAGTCTTTCCTGCAGGGCCAGCCAAAGTATTAGCAACAACCTAC

ACTGGTATCAGCAAAAATCACATGAGTCTCCAAGGCTTCTCATCAAGTAT

GCTTCCCAGTCCATCTCTGGGATCCCCTCCAGGTTCAGTGGCAGTGGATC

AGGGACAGATTTCACTCTCAGTGTCAACAATGTGGGGACTGAAGATTTTG

GAATGTATTTCTGTCAACAGAGTAACAGCTGGCCGCTCACGTTCGGTGCT

GGGACCAAGCTGGAGCTGAAA

The amino acid sequence of the heavy chain variable region of the antibody 066-4.26.14 was as follows (SEQ ID NO: 48):

EVKLVESGGGLVKPGGSLKLSCAASGFTFRSYAMSWVRQTPEKRLEWVAS

ISTTSNTYYPDSVKGRFTTSRDNARNIVYLQMSSLRSDDTAMYYCGRGVI

TNQAWFAYWGQGTLVTVSA

The amino acid sequence of the light chain variable region of the antibody 066-4.26.14 was as follows (SEQ ID NO: 49):

DIVLTQSPATLSVTPGDSVSLSCRASQSISNNLHWYQQKSHESPRLLIKY

ASQSISGIPSRFSGSGSGTDFTLSVNNVGTEDFGMYFCQQSNSWPLTFGA

GTKLELK 2. 066-4.26.14 Mouse-Human Chimeric Antibody Expression Vector Construction The pGS003-hIgG1CH and pGS003-hIgKCL were selected as the expression vectors for constructing the heavy chain and the light chain of the anti-human Aβ mouse-human chimeric antibody, respectively. Using the synthesized 066-4.26.14 mouse antibody sequence as a template, the VH and the VL mouse antibody genes were PCR amplified and cloned into pGS003-hIgG1CH and pGS003-hIgKCL using restriction enzyme digestion and ligation methods to obtain the transient transfection expression vectors pGS003-066-4.26.14-chAbVH-hIgG1CH and pGS003-066-4.26.14-chAbVL-hIgKCL of the mouse-human chimeric antibody.

The amino acid sequence of the heavy chain of the 066-4.26.14 mouse-human chimeric antibody was as follows (SEQ ID NO: 50):

EVKLVESGGGLVKPGGSLKLSCAASGFTFRSYAMSWVRQTPEKRLEWVAS

ISTTSNTYYPDSVKGRFTTSRDNARNIVYLQMSSLRSDDTAMYYCGRGVI

TNQAWFAYWGQGTLVTVSAASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKRVEPKSCDKTHTCPPCPAPELLGGPSVFLFPPKPK

DTLMISRTPEVTCVVVDVSHEDPEVKFNWYVDGVEVHNAKTKPREEQYNS

-continued

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPG

The amino acid sequence of the light chain of the 066-4.26.14 mouse-human chimeric antibody was as follows (SEQ ID NO: 51):

DIVLTQSPATLSVTPGDSVSLSCRASQSISNNLHWYQQKSHESPRLLIKY

ASQSISGIPSRFSGSGSGTDFTLSVNNVGTEDFGMYFCQQSNSWPLTFGA

GTKLELKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

3. Expression by Transient Ttransfection pGS003-066-4.26.14-chAbVH-hIgG1CH and pGS003-066-4.26.14-chAbVL-hIgKCL were subjected to transient expression.

FreeStyle™ 293E cells were used and subjected to transient transfection expression in Freestyle medium. Twenty-four hours before transfection, 30 ml of 293E cells were inoculated at 0.5×10⁶ cells/ml in a 125 ml conical flask, and cultured on a shaker at 130 rpm in a 37° C., 5% CO₂ incubator. During transfection, 60 μl of 293E Fectin was first taken and added to 1 ml of Opti-MEM, mixed well, and incubated at room temperature for 5 minutes; meanwhile, the total plasmid DNA of the recombinant vector in an amount of 30 μg was dissolved in 1 ml of Opti-MEM. Then, the plasmid DNA and 293E Fectin were mixed thoroughly, with a total volume of 2 ml, incubated at room temperature for 15 minutes, and then the whole mixture was added to the cell culture wells, mixed, and incubated in a 37° C., 5% CO₂ incubator on a shaker at 130 rpm for 7 days. The culture broth was centrifuged at a high speed and the supernatant was taken for vacuum filtration with a microporous membrane.

4. Purification of Protein

According to the operating method provided by the manufacturer, Protein A column (Protein Purification Liquid Chromatography System/AKTA Purifier 10, GE) and nickel column were used for purification to obtain the purified mouse-human chimeric antibody 066-4.26.14-chAb, as shown in FIG. 9.

Example 8: Humanization of Antibodies

The mouse antibody 066-4.26.14 was selected for humanization. The humanization process comprised mainly human template search and reshaping.

The main goal of humanization was the FR sequence in the variable region. Using the amino acid sequences of the mouse antibody 066-4.26.14 VH and VL as templates, sequences alignment were performed on the NCBI website, and 5 humanized reference sequences were found, which were used as reference templates for the humanization of antibody FR regions to design the humanized sequences.

The specific sequences of the CDR regions are shown in Table 4, and the sequences of the humanized antibodies after reshaping are shown in Table 5.

TABLE 4

Sequences of CDR regions of 066-4.26.14 antibody

| Antibody | CDR1 sequence | CDR2 sequence | CDR3 sequence |
| --- | --- | --- | --- |
| 066-4.26.14 H chain | SYAMS (SEQ ID NO: 1) | SISTTSNTYYPDSVKG (SEQ ID NO: 2) | GVITNQAWFAY (SEQ ID NO: 3) |
| 066-4.26.14 L chain | RASQSISNNLH (SEQ ID NO: 4) | YASQSIS (SEQ ID NO: 5) | QQSNSWPLT (SEQ ID NO: 6) |

TABLE 5

Humanized sequences of 066-4.26.14 antibody

| | Humanized sequence |
| --- | --- |
| 066-4.26.14H1 | EVQLVESGGGLVKPGGSLRLSCAASGFTFRSYAMSWVRQAPGKGLEWVASISTTSNTYYPDSVKGRFTTSRDNAKNSLYLQMNSLRAEDTAVYYCGRGVITNQAWFAYWGQGTLVTVSS (SEQ ID NO: 15) |
| 066-4.26.14H2 | EVQLVESGGGLVKPGGSLRLSCAASGFTFRSYAMSWVRQTPEKRLEWVASISTTSNTYYPDSVKGRFTTSRDNAKNSVYLQMSSLRAEDTAVYYCGRGVITNQAWFAYWGQGTTVTVSS (SEQ ID NO: 16) |
| 066-4.26.14H3 | EVQLVQSGAEVKKPGESLKISCKGSGYSFRSYAMSWVRQMPGKGLEWVASISTTSNTYYPDSVKGRVTTSRDKSISTAYLQWSSLKASDTAMYYCGRGVITNQAWFAYVVGQGTLVTVSS (SEQ ID NO: 17) |
| 066-4.26.14H4 | EVQLVESGGGLVQPGGSLRLSCAASGFTFRSYAMSWVRQAPGKGLEWVASISTTSNTYYPDSVKGRFTTSRDNAKNSVYLQMSSLRDEDTAMYYCGRGVITNQAWFAYWGQGILVTVSS (SEQ ID NO: 18) |
| 066-4.26.14H5 | EVQLVESGGGLVQPGGSLRLSCVASGFTFRSYAMSWVRQAPGKGLEWVASISTTSNTYYPDSVKGRFTTSRDNSKNTVYLQMSSLRAEDTAVYYCGRGVITNQAWFAYWGQGTLVTVSS (SEQ ID NO: 19) |
| 066-4.26.14L1 | DIVLTQSPATLSVSPGERVTLSCRASQSISNNLHWYQQKSGQAPRLLIKYASQSISGIPSRFSGSGSGTDFTLTISSLQSEDFAVYFCQQSNSWPLTFGGGTQVEIK (SEQ ID NO: 20) |
| 066-4.26.14L2 | DIVLTQSPATLSVSPGERATLSCRASQSISNNLHWYQQKPGQAPRLLIKYASQSISGIPARFSGSGSGTDFTLTISSLQSEDFAVYFCQQSNSWPLTFGGGTKVEIK (SEQ ID NO: 21) |
| 066-4.26.14L3 | DIVLTQSPDFQSVTPKEKVTISCRASQSISNNLHWYQQKPDQSPKLLIKYASQSISGIPSRFSGSGSGTDFTLTINSLEAEDAAAYFCQQSNSWPLTFGPGTKVEIK (SEQ ID NO: 22) |
| 066-4.26.14L4 | EIVLTQSPGTLSLSPGERATLSCRASQSISNNLHWYQQKPGQAPRLLIKYASQSISGIPDRFSGSGSGTDFTLTISRLEPEDFAVYYCQQSNSWPLTFGGGTKVEIK (SEQ ID NO: 23) |
| 066-4.26.14L5 | EIVLTQSPDFQSVTPKEKVTITCRASQSISNNLHWYQQKPDQSPKLLIKYASQSISGVPSRFSGSGSGTDFTLTINSLEAEDAATYYCQQSNSWPLTFGQGTKVEIK (SEQ ID NO: 24) |

066-4.26.14H1
(SEQ ID NO: 25)

```
gaggtgcagctggtggaatcaggaggaggactggtgaagccaggcggatctctgagactgtcttgcgccgccagcggctttaccttt
cagatcttacgccatgtcttgggtccggcaggcaccaggaaaaggactggagtgggtggccagcatcagcaccaccagcaacacctact
accccgacagcgtgaagggcagattcaccaccagccgggacaacgccaagaacagcctgtacctgcagatgaacagcctgagggccg
aggataccgccgtgtactattgcggacggggagtgatcaccaaccaggcttggttcgcctattgggggcagggaacactggtgaccgtgt
ctagc
```

>066-4.26.14H2

(SEQ ID NO: 26)

gaggtgcagctggtggaatcaggaggaggactggtgaagccaggcggatctctgagactgtcttgcgccgccagcggctttacctt cagaagctacgccatgtcttgggtccggcagacaccagagaagagactggagtgggtggcctctatcagcaccaccagcaacacctacta ccccgacagcgtgaagggcagattcaccaccagccgggacaacgccaagaacagcgtgtacctgcagatgagcagcctgagagccga ggacacagcagtgtactattgcggcaggggcgtgatcaccaaccaggcttggttcgcctattgggggcagggaacaaccgtgaccgtgtc tagc

>066-4.26.14H3

(SEQ ID NO: 27)

gaagtgcagctggtgcagagcggagcagaagtgaagaagcccggcgagtccctgaagatctcttgcaagggcagcggctacagc ttcaggagctacgccatgtcttgggtccggcagatgccaggaaaaggactggagtgggtggcctctatcagcaccaccagcaacacctac taccccgacagcgtgaagggcagagtgacaaccagcagggacaagagcatcagcaccgcctacctgcagtggtctagcctgaaggcca gcgataccgccatgtactattgcggccggggagtgatcaccaaccaggcttggttcgcctattgggggcagggaacactggtgaccgtgtc tagc

>066-4.26.14H4

(SEQ ID NO: 28)

gaggtgcagctggtggaatcaggaggaggactggtgcagccaggaggatctctgagactgtcttgcgccgccagcggctttacctt cagatcttacgccatgtcttgggtccggcaggcaccaggaaaaggactggagtgggtggccagcatcagcaccaccagcaacacctact accccgacagcgtgaagggcagattcaccaccagccgggacaacgccaagaacagcgtgtacctgcagatgagcagcctgagggacg aggataccgccatgtactattgcggccggggagtgatcaccaaccaggcttggttcgcctattgggggcagggaatcctggtgaccgtgtc tagc

>066-4.26.14H5

(SEQ ID NO: 29)

gaggtgcagctggtggaatcaggaggaggactggtgcagccaggaggatctctgagactgtcttgcgtggccagcggcttcacctt cagatcttacgccatgtcttgggtccggcaggcaccaggaaaaggactggagtgggtggccagcatcagcaccaccagcaacacctact accccgacagcgtgaagggcagattcaccaccagccgggacaacagcaagaacaccgtgtacctgcagatgagcagcctgagagccg aggacacagcagtgtactattgcggcaggggcgtgatcaccaaccaggcttggttcgcctattgggggcagggaacactggtgaccgtgt ctagc

>066-4.26.14L1

(SEQ ID NO: 30)

gacatcgtgctgacccagtctccagccacactgagcgtgtctccaggagagagagtgaccctgtcttgcagagccagccagagcat cagcaacaacctgcattggtaccagcagaagtccggccaggctcctaggctgctgatcaagtacgccagccagagcattagcggcatccc ttctagattcagcggcagcggaagcggcacagatttcaccctgaccatcagcagcctgcagagcgaggacttcgccgtctacttctgccag cagagcaactcttggcccctgacctttggcggaggcacccaggtggagatcaag

>066-4.26.14L2

(SEQ ID NO: 31)

gacatcgtgctgacccagtctccagccacactgagcgtgtctccaggagagagagccacactgtcttgcagagccagccagagcat cagcaacaacctgcattggtaccagcagaagccaggccaggctcctaggctgctgatcaagtacgcctctcagtctatcagcggcatccca gctagattcagcggcagcggaagcggcacagacttcaccctgaccatcagcagcctgcagagcgaggacttcgccgtctacttctgccag cagagcaactcttggcccctgacctttggcggaggcaccaaggtggagatcaag

>066-4.26.14L3

(SEQ ID NO: 32)

gacatcgtgctgacccagagcccagacttccagtcagtgaccccaaggagaaggtcaccatcagctgcagagccagccagagca tcagcaacaacctgcattggtaccagcagaagcccgaccagagccccaagctgctgatcaagtacgccagccagtctatcagcggcatcc cttctagattcagcggcagcggaagcggcacagatttcaccctgaccatcaacagcctggaggccgaagacgcagccgcctacttttgcc agcagagcaactcttggcccctgacctttggccctggcaccaaggtggagatcaag -continued >066-4.26.14L4
(SEQ ID NO: 33)
gagatcgtgctgacccagtctccaggcacactgtctctgagcccaggagagagagccacactgtcttgcagagccagccagagcat cagcaacaacctgcattggtaccagcagaagccaggccaggctcctaggctgctgatcaagtacgccagccagagcattagcggcatcc cagatagattcagcggcagcggaagcggcacagatttcaccctgaccatcagcagactggagcccgaggacttcgccgtgtactattgcc agcagagcaactcttggcccctgacctttggcggaggcaccaaggtggagatcaag >066-4.26.14L5
(SEQ ID NO: 34)
gagatcgtgctgacccagagcccagacttccagtcagtgaccccaaggagaaggtcaccatcacttgcagggccagccagagca tcagcaacaacctgcattggtaccagcagaagcccgaccagagccccaagctgctgatcaagtacgccagccagtctatcagcggagtg ccttctagattcagcggcagcggaagcggcacagatttcaccctgaccatcaacagcctggaggcagaggacgcagccacctactattgc cagcagagcaactcttggcccctgaccttcggacagggcaccaaggtggagatcaag

Example 9: Preparation of Anti-Aβ Humanized Full-Length Antibody

1. Construction of Expression Vectors for Transient Transfection of Full-Length Antibody The pGS003-hIgG1CH and pGS003-hIgKCL were selected as the expression vectors for constructing the heavy chain and the light chain of the anti-Aβ humanized full-length antibody, respectively. Codon optimization was performed on the 066-4.26.14 humanized antibody sequence. After PCR amplification, the heavy chain was digested with HindIII and NheI, and the light chain was digested with HindIII and NarI, and then 5 VH and 5 VL antibody genes were cloned into pGS003-hIgG1CH and pGS003-hIgKCL, respectively, as shown in Table 6. After sequencing to identify the correct insertion of antibody gene, the recombinant expression vector was transformed into *E. coli* TOP10F', and a single colony was picked and inoculated in LB medium containing 100 μg/ml ampicillin, and cultured with shaking at 37° C. for 16 hours. The plasmids were extracted using endotoxin-free large-scale extraction kit of Zymo Research, and finally the plasmids were dissolved in 1 ml of ultrapure water, and the plasmids concentration and $OD_{260/280}$ were measured with a spectrophotometer. The plasmids DNA with $OD_{260/280}$ between 1.8 and 1.9 were of a relatively high purity.

TABLE 6

List of expression vectors for transient transfection of the heavy chain and the light chain

| Name of Heavy chain expression vector | Name of Light chain expression vector |
|---|---|
| H1 | L1 |
| H2 | L2 |
| H3 | L3 |
| H4 | L4 |
| H5 | L5 |

2. Transfection, Expression and Detection in Mammalian Cells 293E

The above 5 heavy chain expression vectors and 5 light chain expression vectors of 066-4.26.14 were combined in pairs (a total of 25 combinations), and then the transient transfection expression in 2 ml 293E system was evaluated, and the expression levels and ELISA values of the 25 combinations were evaluated. The results are shown in Table 7. Among them, 6 full-length antibodies were preferably selected, which were 066-4.26.14-H2L2, 066-4.26.14-H2L3, 066-4.26.14-H4L2, 066-4.26.14-H5L1, 066-4.26.14-H5L2, 066-4.26.14-H5L3, respectively.

TABLE 7

Detection values of expression level and EC50 for small system transient transfection expression of 066-4.26.14 humanized full-length antibodies of 5 × 5 combination

| No. | Combination of heavy chain and light chain | Expression level (mg/L) | EC50 value of Aβ$_{42}$ monomer |
|---|---|---|---|
| 1 | 066-4.26.14H1L1 | 60 | — |
| 2 | 066-4.26.14H1L2 | 61 | — |
| 3 | 066-4.26.14H1L3 | 68.2 | — |
| 4 | 066-4.26.14H1L4 | 32.1 | — |
| 5 | 066-4.26.14H1L5 | 68.4 | — |
| 6 | 066-4.26.14H2L1 | 89.7 | 0.02135 |
| 7 | 066-4.26.14H2L2 | 86.6 | 0.01291 |
| 8 | 066-4.26.14H2L3 | 51.8 | 0.01532 |
| 9 | 066-4.26.14H2L4 | 7.72 | — |
| 10 | 066-4.26.14H2L5 | 6.14 | — |
| 11 | 066-4.26.14H3L1 | 5.42 | — |
| 12 | 066-4.26.14H3L2 | 0 | — |
| 13 | 066-4.26.14H3L3 | 6.78 | — |
| 14 | 066-4.26.14H3L4 | 3.88 | — |
| 15 | 066-4.26.14H3L5 | 3.68 | — |
| 16 | 066-4.26.14H4L1 | 69.1 | 0.04948 |
| 17 | 066-4.26.14H4L2 | 71.2 | 0.01685 |
| 18 | 066-4.26.14H4L3 | 25.3 | 0.1406 |
| 19 | 066-4.26.14H4L4 | 3.96 | — |
| 20 | 066-4.26.14H4L5 | 0 | — |
| 21 | 066-4.26.14H5L1 | 118.5 | 0.004218 |
| 22 | 066-4.26.14H5L2 | 113.2 | 0.00772 |
| 23 | 066-4.26.14H5L3 | 103.3 | 0.01075 |
| 24 | 066-4.26.14H5L4 | 3.12 | — |
| 25 | 066-4.26.14H5L5 | 0 | — |

Note:
"—" in the table means no combination.

293E was used for transient transfection and expression of 6 candidate antibodies in Freestyle medium. Twenty-four hours before transfection, 300 ml of 293E cells were inoculated at 0.5×10⁶ cells/ml in a 1 L cell culture flask, and cultured in a 37° C., 5% $CO_2$ incubator with a shaker at 120 rpm. During transfection, 300 μl of 293 fectin was firstly taken and added to 5.7 ml of Opti-MEM, mixed well, and incubated at room temperature for 2 minutes; meanwhile, the expression plasmids for the heavy chain and the light chain in amount of 300 μg were diluted to 6 ml with Opti-MEM, respectively. The above-diluted transfection reagent and plasmid were mixed thoroughly, incubated at room temperature for 15 minutes, then the whole mixture was added to the cells, mixed well, and incubated in a 37° C., 5% $CO_2$ incubator with a shaker at 120 rpm for 7 days.

3. Purification and Detection of Antibodies

The cell culture medium was centrifuged at 2000 g for 20 min, the supernatant was collected, and the antibody expression level in the supernatant was detected by Octet. See Table 8.

TABLE 8

Detection of expression level of 6 candidate antibodies expressed by transient transfection in 300 ml

| Antibody name | Heavy chain sequence | Light chain sequence | Expression level of transient transfection (mg/L) |
|---|---|---|---|
| 066-4.26.14H2L2 | 066-4.26.14H2 | 066-4.26.14L2 | 146 |
| 066-4.26.14H2L3 | 066-4.26.14H2 | 066-4.26.14L3 | 56 |
| 066-4.26.14H4L2 | 066-4.26.14H4 | 066-4.26.14L2 | 101 |
| 066-4.26.14H5L1 | 066-4.26.14H5 | 066-4.26.14L1 | 164 |
| 066-4.26.14H5L2 | 066-4.26.14H5 | 066-4.26.14L2 | 128 |
| 066-4.26.14H5L3 | 066-4.26.14H5 | 066-4.26.14L3 | 135 |

Figures 10A, 10B:
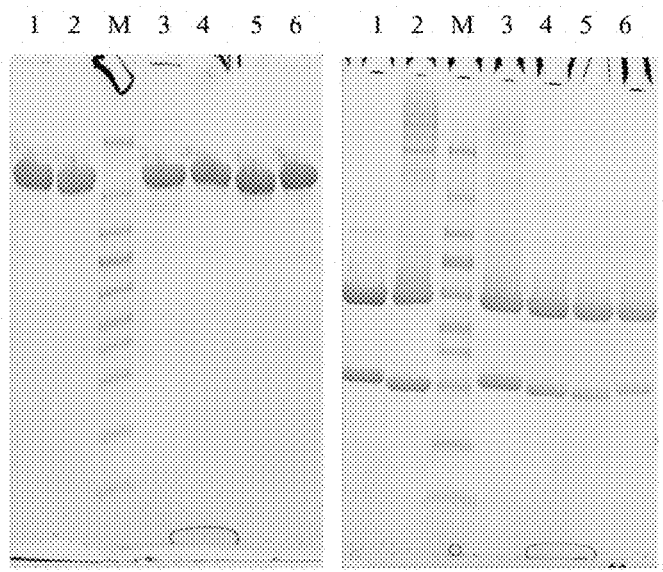
in FIG. 10(A), lanes 1 to 6 are humanized antibodies 066-4.26.14H2L2, 066-4.26.14H2L3, 066-4.26.14H4L2, 066-4.26.14H5L1, 066-4.26.14H5L2, 066-4.26.14H5L3 (non-reducing), respectively.
in FIG. 10(B), lanes 1 to 6 are humanized antibodies 066-4.26.14H2L2, 066-4.26.14H2L3, 066-4.26.14H4L2, 066-4.26.14H5L1, 066-4.26.14H5L2, 066-4.26.14H5L3 (reducing), respectively.

The supernatant was filtered with a 0.22 μm filter, and then passed through a MabSelect SuRe affinity chromatography column (GE), eluted with 20 mM citrate-sodium citrate, pH 3.0, and the pH was adjusted to neutral with 1 M Tris base, and the solution was adjusted to an isotonic solution by adding with 10×PBS. The purified protein was detected by SDS-PAGE with 4-20% gradient gel (Nanjing Jinsirui Biotechnology Co., Ltd.). The results are shown in FIG. 10 below.

Example 10: Determination of EC50 Value of Humanized Candidate Antibody

Coating: The human $A\beta_{42}$ monomer was diluted with CBS (pH 9.4) to 1 μg/ml, added to 96-well microtiter plate, 50 μl per well, and incubated overnight at 2-8° C.

Blocking: After washing the plate three times with PBST, 3% BSA was used for blocking, 200 μl per well, and incubated for 1 hour at 25° C.

Sample processing: The humanized candidate antibody and chimeric antibody were taken respectively, subjected to 2-fold gradient dilution using 10 μg/ml as the starting concentration ($2^0$ to $2^{-11}$), 50 μl/well, and incubated at 25° C. for 1 h.

Addition of antibody: After washing the plate four times with PBST, anti-human IgG (H+L)-HRP antibody in 1:5000 diluent was added, 50 μl/well, and incubated at 25° C. for 1 h.

Color development: After washing the plate four times, TMB color development solution was added, 50 μl per well, and developed in the dark for 3 minutes at room temperature.

Stop: The stop solution was directly added to stop the reaction, 50 μl per well.

Detection: After the reaction was stopped, the microtiter plate was immediately placed into a microplate reader to measure the OD value at 450 nm, and the original data were stored.

Data processing: The raw data were input into the software SoftMax Pro 6.2.1 for data processing. See Table 9 for the specific data. The results showed that the binding capability of the 6 humanized candidate antibodies to human Aβ was equivalent to that of the chimeric antibody.

TABLE 9

EC50 values of 6 candidate antibodies binding to antigen

| Antibody name | EC50 value of $A\beta_{42}$ monomer |
|---|---|
| 066-4.26.14H2L2 | 0.0129 |
| 066-4.26.14H2L3 | 0.0153 |
| 066-4.26.14H4L2 | 0.0168 |
| 066-4.26.14H5L1 | 0.0042 |
| 066-4.26.14H5L2 | 0.0077 |
| 066-4.26.14H5L3 | 0.0108 |
| 066-4.26.14-chAb | 0.0255 |

Example 11: Determination of KD Value of Humanized Candidate Antibody

Biacore-T200 detection was performed, ProteinA chip was used to capture candidate antibodies or positive antibodies, different concentrations of human Aβ antigen were used to flow through the chip, and the fitting analysis was performed based on the collected data. The antigen sample was subjected to 2-fold gradient dilution using HBS-EP+ Buffer to obtain solutions with gradient concentrations of 400 nmol/L, 200 nmol/L, 100 nmol/L, 50 nmol/L, 25 nmol/L, 12.5 nmol/L, 6.25 nmol/L, 3.125 nmol/L, 1.56 nmol/L, 0.78 nmol/L, 0 nmol/L. The sample of 25 nmol/L was used for repeat concentration detection. The detection conditions were: capture time: 30 s; antigen binding time: 120 s; dissociation time: 900 s; flow rate: 30 μl/min. And the regeneration conditions were: 20 mM NaOH solution, flow rate: 30 μl/min. The specific experimental results are shown in Table 10. It could be seen from the experimental results that, compared with the mouse-human chimeric antibody, the KD value of the humanized antibody could be equivalent to that of the mouse antibody.

TABLE 10

KD value detection of 6 candidate antibodies

| Antibody name | Ka (1/Ms) | Kd (1/s) | KD (M) |
|---|---|---|---|
| 066-4.26.14H2L2 | 1.92E+04 | 4.33E−04 | 2.25E−08 |
| 066-4.26.14H2L3 | 1.83E+04 | 4.72E−04 | 2.58E−08 |
| 066-4.26.14H4L2 | 1.28E+04 | 4.63E−04 | 3.63E−08 |
| 066-4.26.14H5L1 | 1.89E+04 | 4.69E−04 | 2.48E−08 |
| 066-4.26.14H5L2 | 1.34E+04 | 2.78E−04 | 2.08E−08 |
| 066-4.26.14H5L3 | 1.42E+04 | 4.60E−04 | 3.25E−08 |
| 066-4.26.14-chAb | 2.65E+04 | 3.33E−04 | 1.26E−08 |

Note:
E+04: ×$10^4$; E−04: ×$10^{-4}$; E−08: ×$10^{-08}$.

Figure 11:
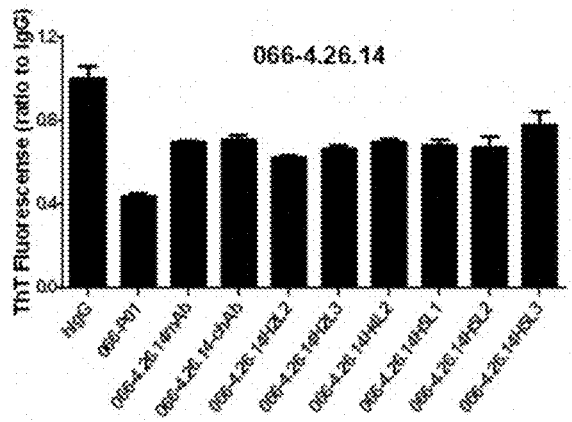
FIG. 11 shows the detection results of humanized Aβ antibodies in inhibiting Aβ polymerization; the abscissa represents different sample groups, and the ordinate represents relative fluorescence intensity; the humanized antibodies of 066-4.26.14 all can inhibit Aβ polymerization.

Example 12: Detection of Effect of Humanized Anti-Aβ Antibody Inhibiting Aβ Polymerization 8.2% DMSO/DPBS solution (DMSO: sigma; DPBS: Hyclone) was used to dissolve Aβ dry powder to 1 mg/ml, DPBS was used to dilute the Aβ solution to 33 μg/ml, and the humanized candidate antibody 066-4.26.14 was diluted to 450 μg/ml (IC100), and ThT (sigma) was diluted to 20 μM with ultrapure water. 50 μl of the candidate antibody diluent was taken and added to 96-well black plate (corning), then added with 50 μl of the Aβ diluent and finally added with 100 μl of ThT, incubated at room temperature for 24 hours in the dark, and measured with a mutifunctional microplate reader to determine fluorescence intensity (Ex/Em=440/485). The abscissa represented different sample groups, and the ordinate represented relative fluorescence intensity. The results are shown in FIG. 11. The relative fluorescence intensity of hIgG was 1.00, the relative fluorescence intensity of the 066-4.26.14-mAb group was 0.70, the relative fluorescence intensity of the 066-4.26.14-chAb group was 0.71, the relative fluorescence intensity of the 066-4.26.14H2L2 group was 0.62, the relative fluorescence intensity of the 066-4.26.14H2L3 group was 0.67, the relative fluorescence intensity of the 066-4.26.14H4L2 group was 0.70, the relative fluorescence intensity of the 066-4.26.14H5L1 group was 0.68, the relative fluorescence intensity of the 066-4.26.14H5L2 group was 0.67, and the relative fluorescence intensity of the 066-4.26.14H5L3 group was 0.78. It could be seen that the humanized antibodies of 066-4.26.14 could inhibit Aβ polymerization.

Figure 12:
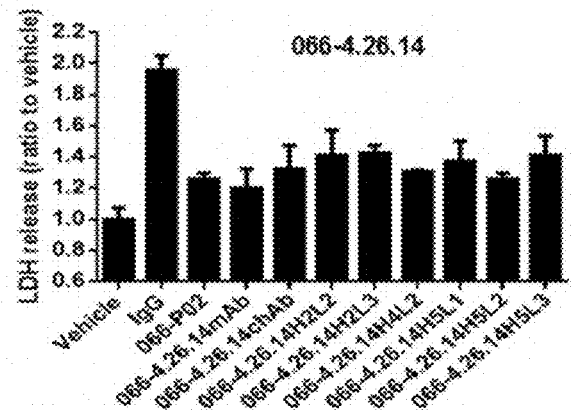
FIG. 12 shows the protective activity detection results of humanized Aβ antibodies against cytotoxicity; the abscissa represents different sample groups, and the ordinate represents relative value of LDH release, the humanized candidate antibodies of 066-4.26.14 all have protective effect against cytotoxicity, and the protective effect is equivalent to that of 066-P02, in which 066-4.26.14H5L2 shows the best performance.

Example 13: Detection of Protective Activity of Humanized Anti-Aβ Antibody Against Cytotoxicity Logarithmic growth phase SHSY5Y cells were digested with 0.25% trypsin, counted, adjusted with EMEM medium (ATCC) containing 10% fetal calf serum to have a cell density of $3 \times 10^4$/ml, inoculated on a 96-well cell culture plate, 100 μl/well; the humanized candidate antibodies of 066-4.26.14 was diluted with EMEM medium containing 1% fetal bovine serum to 200 μg/ml (IC100) and used as working solutions, Aβ was diluted to 240 μg/ml. The culture medium in the culture plate was discarded, 50 μl of the candidate antibody diluent was firstly added, then added with 50 μl of the Aβ diluent, multiple wells were set; incubation was performed in a 37° C., 5% $CO_2$ incubator for 48 hours; 50 μl of the supernatant was taken and added to a new 96-well plate, then added with 50 μl of LDH assay buffer, reacted in the dark at room temperature for 30 minutes, added with 50 μl of stop solution, and measured with a multifunctional microplate reader to determine absorbance. The abscissa represented different sample groups, and the ordinate represented relative value of LDH release. The results are shown in FIG. 12. The relative value of LDH release of hIgG was 1.00, the relative value of LDH release of the 066-P02 group was 1.26, the relative value of LDH release of the 066-4.26.14-mAb group was 1.20, the relative value of LDH release of the 066-4.26.14-chAb group was 1.32, the relative value of LDH release of the 066-4.26.14H2L2 group was 1.41, the relative value of LDH release of the 066-4.26.14H2L3 group was 1.42, the relative value of LDH release of the 066-4.26.14H4L2 group was 1.30, the relative value of LDH release of the 066-4.26.14H5L1 group was 1.37, the relative value of LDH release of the 066-4.26.14H5L2 group was 1.26, and the relative value of LDH release of the 066-4.26.14H5L3 group was 1.41. It could be seen that the humanized candidate antibodies of 066-4.26.14 all had protective effect against cytotoxicity, and the protective effect was equivalent to that of 066-P02, in which the 066-4.26.14H5L2 showed the best performance.

The humanized anti-Aβ monoclonal antibody and its use provided by the present disclosure have been introduced in detail above. The principle and implementation of the present disclosure are illustrated with specific examples, while the description of the above examples is only used to help understand the method and the core idea of the present disclosure. It should be pointed out that for those skilled in the art, without departing from the principle of the present disclosure, several improvements and modifications can be made to the present disclosure, and these improvements and modifications also fall within the protection scope of the claims of the present disclosure.

What is claimed is:

1. An anti-AB humanized monoclonal antibody comprising a heavy chain variable region (VH) comprising three heavy chain CDR regions and a light chain variable region (VL) comprising three light chain CDR regions, wherein amino acid sequence of the three heavy chain CDR regions of the anti-Aβ humanized monoclonal antibody are the amino acid sequences of SEQ ID NOs: 1, 2 and 3, respectively; and wherein amino acid sequences of the three light chain CDR regions of the anti-Aβ humanized monoclonal antibody are the amino acid sequences of SEQ ID NOs: 4, 5 and 6, respectively.

2. The anti-Aβ humanized monoclonal antibody according to claim 1, wherein
the VH has the amino acid sequence of SEQ ID NO: 16, and the VL has the amino acid sequence of SEQ ID NO: 21; or
the VH has the amino acid sequence of SEQ ID NO: 16, and the VL has the amino acid sequence of SEQ ID NO: 22; or
the VH has the amino acid sequence of SEQ ID NO: 18, and the VL has the amino acid sequence of SEQ ID NO: 21; or
the VH has the amino acid sequence of SEQ ID NO: 19, and the VL has the amino acid sequence of SEQ ID NO: 20; or
the VH has the amino acid sequence of SEQ ID NO: 19, and the VL has the amino acid sequence of SEQ ID NO: 21; or
the VH has the amino acid sequence of SEQ ID NO: 19, and the VL has the amino acid sequence of SEQ ID NO: 22.

3. The anti-Aβ humanized monoclonal antibody according to claim 1,
wherein amino acid sequences of four heavy chain framework (FR) regions of the anti-Aβ humanized monoclonal antibody are the amino acid sequences of SEQ ID NOs: 7, 8,9 and 10, respectively; and wherein amino acid sequences of four light chain FR regions of the anti-Aβ humanized monoclonal antibody are the amino acid sequences of SEQ ID NOs: 11, 12, 13 and 14, respectively.

4. The anti-Aβ humanized monoclonal antibody according to claim 1 further comprising a constant region, wherein the anti-Aβ humanized monoclonal antibody has a heavy chain constant region that is of human IgG1, IgG2, IgG3 or IgG4; and a light chain constant region that is of κ type or λ type.

5. The anti-Aβ humanized monoclonal antibody according to claim 2, wherein the anti-Aβ humanized monoclonal antibody further comprises a constant region, wherein the anti-Aβ humanized monoclonal antibody has a heavy chain constant region that is of human IgG1, IgG2, IgG3 or IgG4; and a light chain constant region that is of κ type or λ type.

6. A conjugate comprising the anti-Aβ humanized monoclonal antibody according to claim 1 that is chemically labeled with a chemical label or biologically labeled with a biological label, wherein the chemical label is selected from an isotope or immunotoxin, and wherein the biological label is selected from a biotin, avidin, horseradish peroxidase or alkaline phosphatase.

7. A coupling product, which is prepared by coupling the anti-Aβ humanized monoclonal antibody according to claim 1 or a conjugate thereof with a solid medium or a semi-solid medium, wherein the conjugate comprises the anti-Aβ humanized monoclonal antibody that is chemically labeled with a chemical label or biologically labeled with a biological label, wherein the chemical label is selected from an isotope or immunotoxin, and wherein the biological label is selected from a biotin, avidin, horseradish peroxidase or alkaline phosphatase, and wherein the solid medium or non-solid medium is selected from colloidal gold, polystyrene plates or beads.

8. A medicament comprising the anti-Aβ humanized monoclonal antibody according to claim 1, a conjugate thereof and/or a coupling product thereof; wherein the conjugate comprises the anti-Aβ humanized monoclonal antibody that is chemically labeled with a chemical label or biologically labeled with a biological label, wherein the chemical label is selected from an isotope or immunotoxin, and wherein the biological label is selected from a biotin, avidin, horseradish peroxidase or alkaline phosphatase; and wherein the coupling product is prepared by coupling the anti-Aβ humanized monoclonal antibody or the conjugate with a solid medium or a semi-solid medium, and wherein the solid medium or non-solid medium is selected from colloidal gold, polystyrene plates or beads.

9. A kit, comprising the anti-Aβ humanized monoclonal antibody according to claim 1, a conjugate thereof and/or a coupling product thereof, wherein the conjugate comprises the anti-Aβ humanized monoclonal antibody that is chemically labeled with a chemical label or biologically labeled with a biological label, wherein the chemical label is selected from an isotope or immunotoxin, and wherein the biological label is selected from a biotin, avidin, horseradish peroxidase or alkaline phosphatase; and wherein the coupling product is prepared by coupling the anti-Aβ humanized monoclonal antibody or the conjugate with a solid medium or a semi-solid medium, and wherein the solid medium or non-solid medium is selected from colloidal gold, polystyrene plates or beads.

* * * * *

SEQUENCE LISTING

```
<160> NUMBER OF SEQ ID NOS: 51

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Ser Tyr Ala Met Ser
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic

<400> SEQUENCE: 2

Ser Ile Ser Thr Thr Ser Asn Thr Tyr Tyr Pro Asp Ser Val Lys Gly
1               5                   10                  15

<210> SEQ ID NO 3
<211> LENGTH: 11
<212> TYPE: PRT
<213> ORGANISM: Artificial Sequence
<220> FEATURE:
<223> OTHER INFORMATION: Synthetic
```

```
<400> SEQUENCE: 3

Gly Val Ile Thr Asn Gln Ala Trp Phe Ala Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Arg Ala Ser Gln Ser Ile Ser Asn Asn Leu His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Tyr Ala Ser Gln Ser Ile Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Gln Gln Ser Asn Ser Trp Pro Leu Thr
1               5

<210> SEQ ID NO 7
<211> LENGTH: 30
<212> TYPE: PRT
<213> ORGANISM: Artificial Sequence
<220> FEATURE:
<223> OTHER INFORMATION: Synthetic

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Arg
            20                  25                  30

<210> SEQ ID NO 8
<211> LENGTH: 14
<212> TYPE: PRT
<213> ORGANISM: Artificial Sequence
<220> FEATURE:
<223> OTHER INFORMATION: Synthetic

<400> SEQUENCE: 8

Trp Val Arg Gln Ala Pro Gly Lys Gly Leu Glu Trp Val Ala
1               5                   10

<210> SEQ ID NO 9
<211> LENGTH: 32
<212> TYPE: PRT
<213> ORGANISM: Artificial Sequence
<220> FEATURE:
```

```
<223> OTHER INFORMATION: Synthetic

<400> SEQUENCE: 9

Arg Phe Thr Thr Ser Arg Asp Asn Ser Lys Asn Thr Val Tyr Leu Gln
1               5                   10                  15

Met Ser Ser Leu Arg Ala Glu Asp Thr Ala Val Tyr Tyr Cys Gly Arg
            20                  25                  30

<210> SEQ ID NO 10
<211> LENGTH: 11
<212> TYPE: PRT
<213> ORGANISM: Artificial Sequence
<220> FEATURE:
<223> OTHER INFORMATION: Synthetic

<400> SEQUENCE: 10

Trp Gly Gln Gly Thr Leu Val Thr Val Ser Ser
1               5                   10

<210> SEQ ID NO 11
<211> LENGTH: 23
<212> TYPE: PRT
<213> ORGANISM: Artificial Sequence
<220> FEATURE:
<223> OTHER INFORMATION: Synthetic

<400> SEQUENCE: 11

Asp Ile Val Leu Thr Gln Ser Pro Ala Thr Leu Ser Val Ser Pro Gly
1               5                   10                  15

Glu Arg Ala Thr Leu Ser Cys
            20

<210> SEQ ID NO 12
<211> LENGTH: 15
<212> TYPE: PRT
<213> ORGANISM: Artificial Sequence
<220> FEATURE:
<223> OTHER INFORMATION: Synthetic

<400> SEQUENCE: 12

Trp Tyr Gln Gln Lys Pro Gly Gln Ala Pro Arg Leu Leu Ile Lys
1               5                   10                  15

<210> SEQ ID NO 13
<211> LENGTH: 32
<212> TYPE: PRT
<213> ORGANISM: Artificial Sequence
<220> FEATURE:
<223> OTHER INFORMATION: Synthetic

<400> SEQUENCE: 13

Gly Ile Pro Ala Arg Phe Ser Gly Ser Gly Ser Gly Thr Asp Phe Thr
1               5                   10                  15

Leu Thr Ile Ser Ser Leu Gln Ser Glu Asp Phe Ala Val Tyr Phe Cys
            20                  25                  30

<210> SEQ ID NO 14
<211> LENGTH: 10
<212> TYPE: PRT
<213> ORGANISM: Artificial Sequence
<220> FEATURE:
<223> OTHER INFORMATION: Synthetic

<400> SEQUENCE: 14

Phe Gly Gly Gly Thr Lys Val Glu Ile Lys
```

<210> SEQ ID NO 15
<211> LENGTH: 119
<212> TYPE: PRT
<213> ORGANISM: Artificial Sequence
<220> FEATURE:
<223> OTHER INFORMATION: Synthetic

<400> SEQUENCE: 15

Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Arg Ser Tyr
            20                  25                  30
Ala Met Ser Trp Val Arg Gln Ala Pro Gly Lys Gly Leu Glu Trp Val
        35                  40                  45
Ala Ser Ile Ser Thr Thr Ser Asn Thr Tyr Tyr Pro Asp Ser Val Lys
    50                  55                  60
Gly Arg Phe Thr Thr Ser Arg Asp Asn Ala Lys Asn Ser Leu Tyr Leu
65                  70                  75                  80
Gln Met Asn Ser Leu Arg Ala Glu Asp Thr Ala Val Tyr Tyr Cys Gly
                85                  90                  95
Arg Gly Val Ile Thr Asn Gln Ala Trp Phe Ala Tyr Trp Gly Gln Gly
            100                 105                 110
Thr Leu Val Thr Val Ser Ser
        115

<210> SEQ ID NO 16
<211> LENGTH: 119
<212> TYPE: PRT
<213> ORGANISM: Artificial Sequence
<220> FEATURE:
<223> OTHER INFORMATION: Synthetic

<400> SEQUENCE: 16

Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Arg Ser Tyr
            20                  25                  30
Ala Met Ser Trp Val Arg Gln Thr Pro Glu Lys Arg Leu Glu Trp Val
        35                  40                  45
Ala Ser Ile Ser Thr Thr Ser Asn Thr Tyr Tyr Pro Asp Ser Val Lys
    50                  55                  60
Gly Arg Phe Thr Thr Ser Arg Asp Asn Ala Lys Asn Ser Val Tyr Leu
65                  70                  75                  80
Gln Met Ser Ser Leu Arg Ala Glu Asp Thr Ala Val Tyr Tyr Cys Gly
                85                  90                  95
Arg Gly Val Ile Thr Asn Gln Ala Trp Phe Ala Tyr Trp Gly Gln Gly
            100                 105                 110
Thr Thr Val Thr Val Ser Ser
        115

<210> SEQ ID NO 17
<211> LENGTH: 119
<212> TYPE: PRT
<213> ORGANISM: Artificial Sequence
<220> FEATURE:
<223> OTHER INFORMATION: Synthetic

<400> SEQUENCE: 17

Glu Val Gln Leu Val Gln Ser Gly Ala Glu Val Lys Pro Gly Glu
1               5                   10                  15

Ser Leu Lys Ile Ser Cys Lys Gly Ser Gly Tyr Ser Phe Arg Ser Tyr
            20                  25                  30

Ala Met Ser Trp Val Arg Gln Met Pro Gly Lys Gly Leu Glu Trp Val
        35                  40                  45

Ala Ser Ile Ser Thr Thr Ser Asn Thr Tyr Tyr Pro Asp Ser Val Lys
    50                  55                  60

Gly Arg Val Thr Thr Ser Arg Asp Lys Ser Ile Ser Thr Ala Tyr Leu
65                  70                  75                  80

Gln Trp Ser Ser Leu Lys Ala Ser Asp Thr Ala Met Tyr Tyr Cys Gly
                85                  90                  95

Arg Gly Val Ile Thr Asn Gln Ala Trp Phe Ala Tyr Trp Gly Gln Gly
                100                 105                 110

Thr Leu Val Thr Val Ser Ser
            115

<210> SEQ ID NO 18
<211> LENGTH: 119
<212> TYPE: PRT
<213> ORGANISM: Artificial Sequence
<220> FEATURE:
<223> OTHER INFORMATION: Synthetic

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Leu Glu Trp Val
        35                  40                  45

Ala Ser Ile Ser Thr Thr Ser Asn Thr Tyr Tyr Pro Asp Ser Val Lys
    50                  55                  60

Gly Arg Phe Thr Thr Ser Arg Asp Asn Ala Lys Asn Ser Val Tyr Leu
65                  70                  75                  80

Gln Met Ser Ser Leu Arg Asp Glu Asp Thr Ala Met Tyr Tyr Cys Gly
                85                  90                  95

Arg Gly Val Ile Thr Asn Gln Ala Trp Phe Ala Tyr Trp Gly Gln Gly
                100                 105                 110

Ile Leu Val Thr Val Ser Ser
            115

<210> SEQ ID NO 19
<211> LENGTH: 119
<212> TYPE: PRT
<213> ORGANISM: Artificial Sequence
<220> FEATURE:
<223> OTHER INFORMATION: Synthetic

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Arg Ser Tyr
            20                  25                  30

Ala Met Ser Trp Val Arg Gln Ala Pro Gly Lys Gly Leu Glu Trp Val
        35                  40                  45

Ala Ser Ile Ser Thr Thr Ser Asn Thr Tyr Tyr Pro Asp Ser Val Lys

```
                    50                  55                  60
Gly Arg Phe Thr Thr Ser Arg Asp Asn Ser Lys Asn Thr Val Tyr Leu
 65                  70                  75                  80

Gln Met Ser Ser Leu Arg Ala Glu Asp Thr Ala Val Tyr Tyr Cys Gly
                     85                  90                  95

Arg Gly Val Ile Thr Asn Gln Ala Trp Phe Ala Tyr Trp Gly Gln Gly
                100                 105                 110

Thr Leu Val Thr Val Ser Ser
            115

<210> SEQ ID NO 20
<211> LENGTH: 107
<212> TYPE: PRT
<213> ORGANISM: Artificial Sequence
<220> FEATURE:
<223> OTHER INFORMATION: Synthetic

<400> SEQUENCE: 20

Asp Ile Val Leu Thr Gln Ser Pro Ala Thr Leu Ser Val Ser Pro Gly
  1               5                  10                  15

Glu Arg Val Thr Leu Ser Cys Arg Ala Ser Gln Ser Ile Ser Asn Asn
                 20                  25                  30

Leu His Trp Tyr Gln Gln Lys Ser Gly Gln Ala Pro Arg Leu Leu Ile
             35                  40                  45

Lys Tyr Ala Ser Gln Ser Ile Ser Gly Ile Pro Ser Arg Phe Ser Gly
 50                  55                  60

Ser Gly Ser Gly Thr Asp Phe Thr Leu Thr Ile Ser Ser Leu Gln Ser
 65                  70                  75                  80

Glu Asp Phe Ala Val Tyr Phe Cys Gln Gln Ser Asn Ser Trp Pro Leu
                 85                  90                  95

Thr Phe Gly Gly Gly Thr Gln Val Glu Ile Lys
                100                 105

<210> SEQ ID NO 21
<211> LENGTH: 107
<212> TYPE: PRT
<213> ORGANISM: Artificial Sequence
<220> FEATURE:
<223> OTHER INFORMATION: Synthetic

<400> SEQUENCE: 21

Asp Ile Val Leu Thr Gln Ser Pro Ala Thr Leu Ser Val Ser Pro Gly
  1               5                  10                  15

Glu Arg Ala Thr Leu Ser Cys Arg Ala Ser Gln Ser Ile Ser Asn Asn
                 20                  25                  30

Leu His Trp Tyr Gln Gln Lys Pro Gly Gln Ala Pro Arg Leu Leu Ile
             35                  40                  45

Lys Tyr Ala Ser Gln Ser Ile Ser Gly Ile Pro Ala Arg Phe Ser Gly
 50                  55                  60

Ser Gly Ser Gly Thr Asp Phe Thr Leu Thr Ile Ser Ser Leu Gln Ser
 65                  70                  75                  80

Glu Asp Phe Ala Val Tyr Phe Cys Gln Gln Ser Asn Ser Trp Pro Leu
                 85                  90                  95

Thr Phe Gly Gly Gly Thr Lys Val Glu Ile Lys
                100                 105

<210> SEQ ID NO 22
<211> LENGTH: 107
```

```
<212> TYPE: PRT
<213> ORGANISM: Artificial Sequence
<220> FEATURE:
<223> OTHER INFORMATION: Synthetic

<400> SEQUENCE: 22

Asp Ile Val Leu Thr Gln Ser Pro Asp Phe Gln Ser Val Thr Pro Lys
1               5                   10                  15

Glu Lys Val Thr Ile Ser Cys Arg Ala Ser Gln Ser Ile Ser Asn Asn
            20                  25                  30

Leu His Trp Tyr Gln Gln Lys Pro Asp Gln Ser Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Phe Cys Gln Gln Ser Asn Ser Trp Pro Leu
                85                  90                  95

Thr Phe Gly Pro Gly Thr Lys Val Glu Ile Lys
            100                 105

<210> SEQ ID NO 23
<211> LENGTH: 107
<212> TYPE: PRT
<213> ORGANISM: Artificial Sequence
<220> FEATURE:
<223> OTHER INFORMATION: Synthetic

<400> SEQUENCE: 23

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Asn Ser Trp Pro Leu
                85                  90                  95

Thr Phe Gly Gly Gly Thr Lys Val Glu Ile Lys
            100                 105

<210> SEQ ID NO 24
<211> LENGTH: 107
<212> TYPE: PRT
<213> ORGANISM: Artificial Sequence
<220> FEATURE:
<223> OTHER INFORMATION: Synthetic

<400> SEQUENCE: 24

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asn Asn
            20                  25                  30

Leu His Trp Tyr Gln Gln Lys Pro Asp Gln Ser Pro Lys Leu Leu Ile
        35                  40                  45

Lys Tyr Ala Ser Gln Ser Ile Ser Gly Val Pro Ser Arg Phe Ser Gly
```

```
                50              55              60
Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Gln Ser Asn Ser Trp Pro Leu
                 85                  90                  95

Thr Phe Gly Gln Gly Thr Lys Val Glu Ile Lys
            100                 105
```

<210> SEQ ID NO 25
<211> LENGTH: 357
<212> TYPE: DNA
<213> ORGANISM: Artificial Sequence
<220> FEATURE:
<223> OTHER INFORMATION: Synthetic

<400> SEQUENCE: 25

```
gaggtgcagc tggtggaatc aggaggagga ctggtgaagc caggcggatc tctgagactg    60
tcttgcgccg ccagcggctt taccttcaga tcttacgcca tgtcttgggt ccggcaggca   120
ccaggaaaag gactggagtg ggtggccagc atcagcacca ccagcaacac ctactacccc   180
gacagcgtga aggcagatt caccaccagc cgggacaacg ccaagaacag cctgtacctg    240
cagatgaaca gcctgagggc cgaggatacc gccgtgtact attgcggacg gggagtgatc   300
accaaccagg cttggttcgc ctattggggg cagggaacac tggtgaccgt gtctagc      357
```

<210> SEQ ID NO 26
<211> LENGTH: 357
<212> TYPE: DNA
<213> ORGANISM: Artificial Sequence
<220> FEATURE:
<223> OTHER INFORMATION: Synthetic

<400> SEQUENCE: 26

```
gaggtgcagc tggtggaatc aggaggagga ctggtgaagc caggcggatc tctgagactg    60
tcttgcgccg ccagcggctt taccttcaga agctacgcca tgtcttgggt ccggcagaca   120
ccagagaaga gactggagtg ggtggcctct atcagcacca ccagcaacac ctactacccc   180
gacagcgtga aggcagatt caccaccagc cgggacaacg ccaagaacag cgtgtacctg    240
cagatgagca gcctgagagc cgaggacaca gcagtgtact attgcggcag ggcgtgatc    300
accaaccagg cttggttcgc ctattggggg cagggaacaa ccgtgaccgt gtctagc      357
```

<210> SEQ ID NO 27
<211> LENGTH: 357
<212> TYPE: DNA
<213> ORGANISM: Artificial Sequence
<220> FEATURE:
<223> OTHER INFORMATION: Synthetic

<400> SEQUENCE: 27

```
gaagtgcagc tggtgcagag cggagcagaa gtgaagaagc ccggcgagtc cctgaagatc    60
tcttgcaagg gcagcggcta cagcttcagg agctacgcca tgtcttgggt ccggcagatg   120
ccaggaaaag gactggagtg ggtggcctct atcagcacca ccagcaacac ctactacccc   180
gacagcgtga aggcagagt gacaaccagc agggacaaga gcatcagcac cgcctacctg   240
cagtggtcta gcctgaaggc cagcgatacc gccatgtact attgcggccg gggagtgatc   300
accaaccagg cttggttcgc ctattggggg cagggaacac tggtgaccgt gtctagc      357
```

<210> SEQ ID NO 28

```
<211> LENGTH: 357
<212> TYPE: DNA
<213> ORGANISM: Artificial Sequence
<220> FEATURE:
<223> OTHER INFORMATION: Synthetic

<400> SEQUENCE: 28
gaggtgcagc tggtggaatc aggaggagga ctggtgcagc caggaggatc tctgagactg      60
tcttgcgccg ccagcggctt taccttcaga tcttacgcca tgtcttgggt ccggcaggca     120
ccaggaaaag gactggagtg ggtggccagc atcagcacca ccagcaacac ctactacccc     180
gacagcgtga agggcagatt caccaccagc cgggacaacg ccaagaacag cgtgtacctg     240
cagatgagca gcctgaggga cgaggatacc gccatgtact attgcggccg gggagtgatc     300
accaaccagg cttggttcgc ctattggggg cagggaatcc tggtgaccgt gtctagc        357

<210> SEQ ID NO 29
<211> LENGTH: 357
<212> TYPE: DNA
<213> ORGANISM: Artificial Sequence
<220> FEATURE:
<223> OTHER INFORMATION: Synthetic

<400> SEQUENCE: 29
gaggtgcagc tggtggaatc aggaggagga ctggtgcagc caggaggatc tctgagactg      60
tcttgcgtgg ccagcggctt caccttcaga tcttacgcca tgtcttgggt ccggcaggca     120
ccaggaaaag gactggagtg ggtggccagc atcagcacca ccagcaacac ctactacccc     180
gacagcgtga agggcagatt caccaccagc cgggacaaca gcaagaacac cgtgtacctg     240
cagatgagca gcctgagagc cgaggacaca gcagtgtact attgcggcag ggcgtgatc      300 accaaccagg cttggttcgc ctattggggg cagggaacac tggtgaccgt gtctagc        357

<210> SEQ ID NO 30
<211> LENGTH: 321
<212> TYPE: DNA
<213> ORGANISM: Artificial Sequence
<220> FEATURE:
<223> OTHER INFORMATION: Synthetic

<400> SEQUENCE: 30
gacatcgtgc tgacccagtc tccagccaca ctgagcgtgt ctccaggaga gagagtgacc      60
ctgtcttgca gagccagcca gagcatcagc aacaacctgc attggtacca gcagaagtcc     120
ggccaggctc ctaggctgct gatcaagtac gccagccaga gcattagcgg catcccttct     180
agattcagcg gcagcggaag cggcacagat ttcaccctga ccatcagcag cctgcagagc     240
gaggacttcg ccgtctactt ctgccagcag agcaactctt ggccccctgac ctttggcgga    300 ggcacccagg tggagatcaa g                                              321

<210> SEQ ID NO 31
<211> LENGTH: 321
<212> TYPE: DNA
<213> ORGANISM: Artificial Sequence
<220> FEATURE:
<223> OTHER INFORMATION: Synthetic

<400> SEQUENCE: 31
gacatcgtgc tgacccagtc tccagccaca ctgagcgtgt ctccaggaga gagagccaca      60
ctgtcttgca gagccagcca gagcatcagc aacaacctgc attggtacca gcagaagcca     120
ggccaggctc ctaggctgct gatcaagtac gcctctcagt ctatcagcgg catcccagct     180
```

```
agattcagcg gcagcggaag cggcacagac ttcaccctga ccatcagcag cctgcagagc      240
gaggacttcg ccgtctactt ctgccagcag agcaactctt ggcccctgac ctttggcgga      300
ggcaccaagg tggagatcaa g                                                321
```

<210> SEQ ID NO 32
<211> LENGTH: 321
<212> TYPE: DNA
<213> ORGANISM: Artificial Sequence
<220> FEATURE:
<223> OTHER INFORMATION: Synthetic

<400> SEQUENCE: 32

```
gacatcgtgc tgacccagag cccagacttc cagtcagtga cccccaagga gaaggtcacc      60
atcagctgca gagccagcca gagcatcagc aacaacctgc attggtacca gcagaagccc     120
gaccagagcc ccaagctgct gatcaagtac gccagccagt ctatcagcgg catcccttct     180
agattcagcg gcagcggaag cggcacagat ttcaccctga ccatcaacag cctggaggcc     240
gaagacgcag ccgcctactt tgccagcag agcaactctt ggcccctgac ctttggccct      300
ggcaccaagg tggagatcaa g                                                321
```

<210> SEQ ID NO 33
<211> LENGTH: 321
<212> TYPE: DNA
<213> ORGANISM: Artificial Sequence
<220> FEATURE:
<223> OTHER INFORMATION: Synthetic

<400> SEQUENCE: 33

```
gagatcgtgc tgacccagtc tccaggcaca ctgtctctga gcccaggaga gagagccaca      60
ctgtcttgca gagccagcca gagcatcagc aacaacctgc attggtacca gcagaagcca     120
ggccaggctc ctaggctgct gatcaagtac gccagccaga gcattagcgg catcccagat     180
agattcagcg gcagcggaag cggcacagat ttcaccctga ccatcagcag actggagccc     240
gaggacttcg ccgtgtacta ttgccagcag agcaactctt ggcccctgac ctttggcgga     300
ggcaccaagg tggagatcaa g                                                321
```

<210> SEQ ID NO 34
<211> LENGTH: 321
<212> TYPE: DNA
<213> ORGANISM: Artificial Sequence
<220> FEATURE:
<223> OTHER INFORMATION: Synthetic

<400> SEQUENCE: 34

```
gagatcgtgc tgacccagag cccagacttc cagtcagtga cccccaagga gaaggtcacc      60
atcacttgca gggccagcca gagcatcagc aacaacctgc attggtacca gcagaagccc     120
gaccagagcc ccaagctgct gatcaagtac gccagccagt ctatcagcgg agtgccttct     180
agattcagcg gcagcggaag cggcacagat ttcaccctga ccatcaacag cctggaggca     240
gaggacgcag ccacctacta ttgccagcag agcaactctt ggcccctgac cttcggacag     300
ggcaccaagg tggagatcaa g                                                321
```

<210> SEQ ID NO 35
<211> LENGTH: 42
<212> TYPE: PRT
<213> ORGANISM: Artificial Sequence
<220> FEATURE:

<223> OTHER INFORMATION: Synthetic

<400> SEQUENCE: 35

```
Asp Ala Glu Phe Arg His Asp Ser Gly Tyr Glu Val His His Gln Lys
1               5                   10                  15
Leu Val Phe Phe Ala Glu Asp Val Gly Ser Asn Lys Gly Ala Ile Ile
            20                  25                  30
Gly Leu Met Val Gly Gly Val Val Ile Ala
        35                  40
```

<210> SEQ ID NO 36
<211> LENGTH: 16
<212> TYPE: PRT
<213> ORGANISM: Artificial Sequence
<220> FEATURE:
<223> OTHER INFORMATION: Synthetic

<400> SEQUENCE: 36

```
Asp Ala Glu Phe Arg His Asp Ser Gly Tyr Glu Val His His Gln Lys
1               5                   10                  15
```

<210> SEQ ID NO 37
<211> LENGTH: 17
<212> TYPE: PRT
<213> ORGANISM: Artificial Sequence
<220> FEATURE:
<223> OTHER INFORMATION: Synthetic

<400> SEQUENCE: 37

```
His Gln Lys Leu Val Phe Phe Ala Glu Asp Val Gly Ser Asn Lys Gly
1               5                   10                  15
Ala
```

<210> SEQ ID NO 38
<211> LENGTH: 112
<212> TYPE: PRT
<213> ORGANISM: Artificial Sequence
<220> FEATURE:
<223> OTHER INFORMATION: Synthetic

<400> SEQUENCE: 38

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Arg Tyr
            20                  25                  30
Ser Met Ser Trp Val Arg Gln Ala Pro Gly Lys Gly Leu Glu Leu Val
        35                  40                  45
Ala Gln Ile Asn Ser Val Gly Asn Ser Thr Tyr Tyr Pro Asp Thr Val
    50                  55                  60
Lys Gly Arg Phe Thr Ile Ser Arg Asp Asn Ala Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Ser Gly Asp Tyr Trp Gly Gln Gly Thr Leu Val Thr Val Ser Ser
            100                 105                 110
```

<210> SEQ ID NO 39
<211> LENGTH: 112
<212> TYPE: PRT
<213> ORGANISM: Artificial Sequence
<220> FEATURE:
<223> OTHER INFORMATION: Synthetic

<400> SEQUENCE: 39

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Ile Tyr Ser
            20                  25                  30

Asp Gly Asn Ala Tyr Leu His Trp Phe Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

<210> SEQ ID NO 40
<211> LENGTH: 124
<212> TYPE: PRT
<213> ORGANISM: Artificial Sequence
<220> FEATURE:
<223> OTHER INFORMATION: Synthetic

<400> SEQUENCE: 40

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val
        35                  40                  45

Ala Val Ile Trp Phe Asp Gly Thr Lys Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Thr Leu Arg Ala Glu Asp Thr Ala Val Tyr Tyr Cys
                85                  90                  95

Ala Arg Asp Arg Gly Ile Gly Ala Arg Arg Gly Pro Tyr Tyr Met Asp
            100                 105                 110

Val Trp Gly Lys Gly Thr Thr Val Thr Val Ser Ser
        115                 120

<210> SEQ ID NO 41
<211> LENGTH: 107
<212> TYPE: PRT
<213> ORGANISM: Artificial Sequence
<220> FEATURE:
<223> OTHER INFORMATION: Synthetic

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Val Glu Ile Lys
            100                 105
```

```
<210> SEQ ID NO 42
<211> LENGTH: 21
<212> TYPE: DNA
<213> ORGANISM: Artificial Sequence
<220> FEATURE:
<223> OTHER INFORMATION: Synthetic

<400> SEQUENCE: 42
ctcagggaar tarccyttga c                                              21

<210> SEQ ID NO 43
<211> LENGTH: 21
<212> TYPE: DNA
<213> ORGANISM: Artificial Sequence
<220> FEATURE:
<223> OTHER INFORMATION: Synthetic

<400> SEQUENCE: 43
tcactgccat caatcttcca c                                              21

<210> SEQ ID NO 44
<211> LENGTH: 18
<212> TYPE: DNA
<213> ORGANISM: Artificial Sequence
<220> FEATURE:
<223> OTHER INFORMATION: Synthetic

<400> SEQUENCE: 44
tgtaaaacga cggccagt                                                  18

<210> SEQ ID NO 45
<211> LENGTH: 18
<212> TYPE: DNA
<213> ORGANISM: Artificial Sequence
<220> FEATURE:
<223> OTHER INFORMATION: Synthetic

<400> SEQUENCE: 45
caggaaacag ctatgacc                                                  18

<210> SEQ ID NO 46
<211> LENGTH: 357
<212> TYPE: DNA
<213> ORGANISM: Artificial Sequence
<220> FEATURE:
<223> OTHER INFORMATION: Synthetic

<400> SEQUENCE: 46
gaagtgaagc tggtggagtc tgggggaggc ttagtgaagc ctggagggtc cctgaaactc      60
tcctgtgcag cctctggatt cactttcaga agtyatgcca tgtcttgggt tcgccagact     120
ccagagaaga ggctggagtg ggtcgcatcc attagtacta ctagtaacac ctactatcca     180
gacagtgtga aggccgatt caccacctcc agagataacg ccaggaacat cgtgtacctg     240
caaatgagca gtctgaggtc tgacgacacg gccatgtatt actgtggaag aggcgtgatt     300
acgaaccagg cctggtttgc ttactggggc caagggactc tggtcactgt ctctgca        357
```

<210> SEQ ID NO 47
<211> LENGTH: 321
<212> TYPE: DNA
<213> ORGANISM: Artificial Sequence
<220> FEATURE:
<223> OTHER INFORMATION: Synthetic

<400> SEQUENCE: 47

```
gatattgtgc taactcagtc tccagccacc ctgtctgtga ctccaggaga tagcgtcagt    60
ctttcctgca gggccagcca agtattagc aacaacctac actggtatca gcaaaaatca   120
catgagtctc caaggcttct catcaagtat gcttcccagt ccatctctgg gatcccctcc   180
aggttcagtg gcagtggatc aggacagat tcactctca gtgtcaacaa tgtggggact    240
gaagattttg aatgtatttt ctgtcaacag agtaacagct ggccgctcac gttcggtgct   300
gggaccaagc tggagctgaa a                                              321
```

<210> SEQ ID NO 48
<211> LENGTH: 119
<212> TYPE: PRT
<213> ORGANISM: Artificial Sequence
<220> FEATURE:
<223> OTHER INFORMATION: Synthetic

<400> SEQUENCE: 48

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Arg Ser Tyr
            20                  25                  30

Ala Met Ser Trp Val Arg Gln Thr Pro Glu Lys Arg Leu Glu Trp Val
        35                  40                  45

Ala Ser Ile Ser Thr Thr Ser Asn Thr Tyr Tyr Pro Asp Ser Val Lys
    50                  55                  60

Gly Arg Phe Thr Thr Ser Arg Asp Asn Ala Arg Asn Ile Val Tyr Leu
65                  70                  75                  80

Gln Met Ser Ser Leu Arg Ser Asp Asp Thr Ala Met Tyr Tyr Cys Gly
                85                  90                  95

Arg Gly Val Ile Thr Asn Gln Ala Trp Phe Ala Tyr Trp Gly Gln Gly
            100                 105                 110

Thr Leu Val Thr Val Ser Ala
        115
```

<210> SEQ ID NO 49
<211> LENGTH: 107
<212> TYPE: PRT
<213> ORGANISM: Artificial Sequence
<220> FEATURE:
<223> OTHER INFORMATION: Synthetic

<400> SEQUENCE: 49

```
Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60
```

```
Ser Gly Ser Gly Thr Asp Phe Thr Leu Ser Val Asn Asn Val Gly Thr
 65                  70                  75                  80

Glu Asp Phe Gly Met Tyr Phe Cys Gln Gln Ser Asn Ser Trp Pro Leu
                 85                  90                  95

Thr Phe Gly Ala Gly Thr Lys Leu Glu Leu Lys
            100                 105

<210> SEQ ID NO 50
<211> LENGTH: 448
<212> TYPE: PRT
<213> ORGANISM: Artificial Sequence
<220> FEATURE:
<223> OTHER INFORMATION: Synthetic

<400> SEQUENCE: 50

Glu Val Lys Leu Val Glu Ser Gly Gly Gly Leu Val Lys Pro Gly Gly
  1               5                  10                  15

Ser Leu Lys Leu Ser Cys Ala Ala Ser Gly Phe Thr Phe Arg Ser Tyr
                 20                  25                  30

Ala Met Ser Trp Val Arg Gln Thr Pro Glu Lys Arg Leu Glu Trp Val
             35                  40                  45

Ala Ser Ile Ser Thr Thr Ser Asn Thr Tyr Tyr Pro Asp Ser Val Lys
         50                  55                  60

Gly Arg Phe Thr Thr Ser Arg Asp Asn Ala Arg Asn Ile Val Tyr Leu
 65                  70                  75                  80

Gln Met Ser Ser Leu Arg Ser Asp Asp Thr Ala Met Tyr Tyr Cys Gly
                 85                  90                  95

Arg Gly Val Ile Thr Asn Gln Ala Trp Phe Ala Tyr Trp Gly Gln Gly
                100                 105                 110

Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 51
<211> LENGTH: 214
<212> TYPE: PRT
<213> ORGANISM: Artificial Sequence
<220> FEATURE:
<223> OTHER INFORMATION: Synthetic

<400> SEQUENCE: 51

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Val Asn Asn Val Gly Thr
65                  70                  75                  80

Glu Asp Phe Gly Met Tyr Phe Cys Gln Gln Ser Asn Ser Trp Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```